US006693137B1

(12) United States Patent
Arnold et al.

(10) Patent No.: US 6,693,137 B1
(45) Date of Patent: *Feb. 17, 2004

(54) SULPHONAMIDE DERIVATIVES

(75) Inventors: Macklin Brian Arnold, Morgantown, IN (US); David Michael Bender, Indianapolis, IN (US); Buddy Eugene Cantrell, Fountaintown, IN (US); Winton Dennis Jones, Carmel, IN (US); Paul Leslie Ornstein, Carmel, IN (US); Richard Lee Simon, Greenwood, IN (US); Edward C. R. Smith, Fishers, IN (US); Eric George Tromiczak, Indianapolis, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/744,418

(22) PCT Filed: Jul. 28, 1999

(86) PCT No.: PCT/US99/16962

§ 371 (c)(1),
(2), (4) Date: Jan. 23, 2001

(87) PCT Pub. No.: WO00/06148

PCT Pub. Date: Feb. 10, 2000

Related U.S. Application Data

(60) Provisional application No. 60/094,973, filed on Jul. 31, 1998.

(51) Int. Cl.[7] .................. A61K 31/18; A61K 31/22; A61K 31/235; A61K 31/40; A61K 31/505

(52) U.S. Cl. .................. 514/605; 514/252.12; 514/274; 514/331; 514/347; 514/428; 514/524; 514/542; 514/546; 544/311; 544/410; 546/233; 546/293; 548/568; 558/413; 560/13; 560/252; 564/99

(58) Field of Search ................. 514/534, 605, 514/252.12, 274, 331, 347, 428, 524, 542, 546; 562/430; 564/99; 544/311, 400; 546/233, 293; 548/568; 558/413; 560/13, 252

(56) References Cited

U.S. PATENT DOCUMENTS

| 4,443,477 A | * | 4/1984 | Witte et al. ................. 424/319 |
|---|---|---|---|
| 4,948,809 A | | 8/1990 | Witte et al. ................. 514/538 |
| 5,103,054 A | | 4/1992 | Gatto ........................... 564/99 |
| 6,174,922 B1 | | 1/2001 | Arnold et al. ............... 514/604 |

FOREIGN PATENT DOCUMENTS

| EP | 0 655 442 B1 | 11/1993 |
|---|---|---|
| JP | WO 96/25926 | 2/1995 |
| WO | WO 98/33496 | 2/1997 |
| WO | WO 00/06083 | 7/1998 |
| WO | WO 00/06157 | 7/1998 |
| WO | WO 00/06158 | 7/1998 |
| WO | WO 00/06159 | 7/1998 |
| WO | WO 00/06537 | 7/1998 |
| WO | WO 00/66546 | 4/1999 |

* cited by examiner

Primary Examiner—Peter O'Sullivan
(74) Attorney, Agent, or Firm—John A. Cleveland, Jr.; Nelsen L. Lentz

(57) ABSTRACT

The present invention relates to the potentiation of glutamate receptor function using certain sulphonamide derivatives. It also relates to novel sulphonamide derivatives, to processes for their preparation and to pharmaceutical compositions containing them.

13 Claims, No Drawings

SULPHONAMIDE DERIVATIVES

This is a 371 of PCT/US99/16962 filed Jul. 28, 1999 which claims priority to U.S. Provisional Application No. 60/094,973 filed Jul. 31, 1998.

The present invention relates to the potentiation of glutamate receptor function using certain sulphonamide derivatives. It also relates to novel sulphonamide derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are unknown.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulphonamides, S-oxides and homologs which are said to potentiate membrane currents induced by kainic acid and AMPA.

Ampakines have been shown to improve memory in a variety of animal tests. Staubli et al., *Proc. Natl. Acad. Sci.*, Vol. 91, pp 777–781, 1994, *Neurobiology*, and Arai et al., *The Journal of Pharmacology and Experimental Therapeutics*, 278: 627–638, 1996.

It has now been found that cyclothiazide and certain sulphonamide derivatives potentiate agonist-induced excitability of human GluR4B receptor expressed in HEK 293 cells. Since cyclothiazide is known to potentiate glutamate receptor function in vivo, it is believed that this finding portends that the sulphonamide derivatives will also potentiate glutamate receptor function in vivo, and hence that the compounds will exhibit ampakine-like behavior.

In addition, certain sulfonamide derivatives which potentiate glutamate receptor function in a mammal have been disclosed in International Patent Application Publication WO 98/33496 published Aug. 6, 1998.

Accordingly, the present invention provides a compound of the formula:

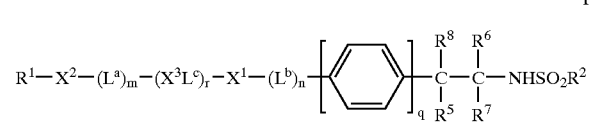

I wherein:
  $L^a$ represents (1–4C)alkylene;
  $L^b$ represents (1–4C)alkylene;
  $L^c$ represents (1–4C)alkylene;
  r is zero or 1;
  m is zero or 1;
  n is zero or 1;
  q is 1 or 2;
  $X^1$ represents O, S, $NR^9$, C(=O), OCO, COO, $NHCO_2$, $O_2CNH$, CONH, NHCO, SO or $SO_2$;
  $X^2$ represents O, S, $NR^{10}$, C(=O), OCO, COO, $NHCO_2$, $O_2CNH$, CONH, NHCO, SO or $SO_2$;
  $X^3$ represents O, S, $NR^{11}$, C(=O), $NHCO_2$, $O_2CNH$, CONH, NHCO, SO or $SO_2$;
  $R^1$ represents a hydrogen atom, a (1–4C)alkyl group, a (3–8C)cycloalkyl group, an optionally substituted aromatic group, an optionally substituted heteroaromatic group, or a saturated 4 to 7 membered heterocyclic ring containing the group $NR^{10}$ and a group X as the only hetero ring members, wherein X represents $—CH_2—$, CO, O, S or $NR^{12}$ and $R^{12}$ represents hydrogen or (1–4C);

$R^9$ is hydrogen or (1–4C)alkyl;

$R^{10}$ is hydrogen or (1–4C)alkyl, or $R^1$ and $R^{10}$ together with the nitrogen atom to which they are attached form an azetidinyl, pyrrolidinyl, piperidinyl, 4-di(1–4C)alkylaminopiperidinyl, morpholino, piperazinyl or N-(1–4C)alkylpiperazinyl group;

$R^{11}$ is hydrogen or (1–4C)alkyl;

$R^2$ represents (1–6C)alkyl, (3–6C)cycloalkyl, (1–6C) fluoroalkyl, (1–6C)chloroalkyl, (2–6C)alkenyl, (1–4C) alkoxy(1–4C)alkyl, phenyl which is unsubstituted or substituted by halogen, (1–4C)alkyl or (1–4C)alkoxy, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; and either one of $R^5$, $R^6$, $R^7$ and $R^8$ represents hydrogen; (1–6C)alkyl; aryl(1–6C)alkyl; (2–6C)alkenyl; aryl (2–6C)alkenyl or aryl, or two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof, provided that (1) if m represents zero, then $X^1$ represents C(=O), CONH, or $SO_2$, $X^2$ represents $NR^{10}$ and $R^1$ and $R^{10}$ together with the nitrogen atom to which they are attached form an azetidinyl, piperidinyl, 4-di(1–4C) alkylaminopiperidinyl, piperazinyl or N-(1–4C) alkylpiperazinyl group, and (2) if the group

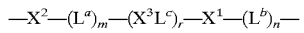

represents $—OCH_2CONH—$, then $R^1$ does not represent an optionally substituted aromatic group or an optionally substituted heteroaromatic group.

According to another aspect, the present invention provides a method of potentiating glutamate receptor function in a mammal (including a human) requiring such treatment, which comprises administering an effective amount of a compound of formula I, or a pharmaceutically acceptable salt thereof as defined herein.

According to another aspect, the present invention provides the use of a compound of formula I, or a pharmaceutically acceptable salt thereof as defined herein for the manufacture of a medicament for potentiating glutamate receptor function.

According to yet another aspect, the present invention provides the use of a compound of formula I or a pharmaceutically acceptable salt thereof as defined herein for potentiating glutamate receptor function.

More specifically, it is understood that the following formulas Ia and Ib are included within the scope of formula I:

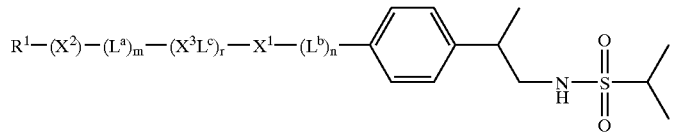

Formula Ia

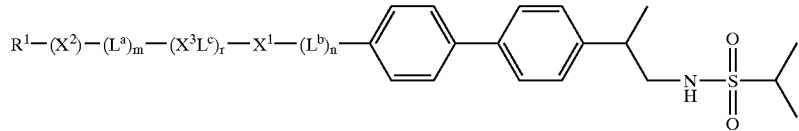

Formula Ib

In this specification, the term "potentiating glutamate receptor function" refers to any increased responsiveness of glutamate receptors, for example AMPA receptors, to glutamate or an agonist, and includes but is not limited to inhibition of rapid desensitisation or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders; neuro-degenerative disorders such as Alzheimer's disease; age-related dementias; age-induced memory impairment; movement disorders such as tardive dyskinesia, Hungtington's chorea, myoclonus and Parkinson's disease; reversal of drug-induced states (such as cocaine, amphetamines, alcohol-induced states); depression; attention deficit disorder; attention deficit hyperactivity disorder; psychosis; cognitive deficits associated with psychosis; and drug-induced psychosis. The compounds of formula I may be further useful for the treatment of sexual dysfunction. The compounds of formula I may also be useful for improving memory (both short term and long term) and learning ability. The present invention provides the use of compounds of formula I for the treatment of each of these conditions.

The term "treating" (or "treat") as used herein includes its generally accepted meaning which encompasses prohibiting, preventing, restraining, and slowing, stopping, or reversing progression, severity, or a resultant symptom.

The present invention includes the pharmaceutically acceptable salts of the compounds defined by formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, g-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aromatic group" means the same as "aryl", and includes phenyl and a polycyclic aromatic carbocyclic ring such as naphthyl.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl and quinolyl.

An optionally substituted aromatic, an optionally substituted (1–4C)alkylaromatic group, or heteroaromatic group may be unsubstituted or substituted by one or two substituents selected from halogen; nitro; cyano; (1–4C)alkyl; (1–4C)alkoxy; halo(1–4C)alkyl; (1–4C)alkanoyl; amino; (1–4C)alkylamino; di(1–4C)alkylamino and (2–4C)alkanoylamino.

Examples of particular values for a saturated 4 to 7 membered heterocyclic ring are azetidinyl, pyrrolidinyl, piperidinyl, morpholinyl, thiomorpholinyl, piperazinyl, hexahydropyrimidyl, tetrahydro-1,3-oxazinyl, tetrahydro-1,3-thiazinyl and hexahydroazepinyl.

The term (1–6C)alkyl includes (1–4C)alkyl. Particular values are methyl, ethyl, propyl, isopropyl, butyl, isobutyl, t-butyl, pentyl and hexyl.

The term (1–4C)alkoxy includes methoxy, ethoxy, propoxy, isopropoxy, butoxy, t-butoxy, and the like.

The term (2–6C)alkenyl includes (3–6C)alkenyl. Particular values are vinyl and prop-2-enyl.

The term (3–8C)cycloalkyl, as such or in the term (3–8C)cycloalkyloxy, includes monocyclic and polycyclic groups. Particular values are cyclopropyl, cyclobutyl, cyclopentyl, cyclohexyl and bicyclo[2.2.2]octane. The term includes (3–6C)cycloalkyl: cyclopropyl, cyclobutyl, cyclopentyl and cyclohexyl.

The term halogen includes fluorine, chlorine, bromine and iodine.

The terms haloalkyl and halo(1–6C)alkyl, include fluoro(1–6C)alkyl, such as trifluoromethyl and 2,2,2-trifluoroethyl, and chloro(1–6C)alkyl such as chloromethyl.

The term (1–4C)alkoxy(1–4C)alkoxy includes methoxymethyl.

The term (1–4C)alkylene includes ethylene, propylene and butylene.

The term thienyl includes thien-2-yl and thien-3-yl.

The term furyl includes fur-2-yl and fur-3-yl.

The term oxazolyl includes oxazol-2-yl, oxazol-4-yl and oxazol-5-yl.

The term isoxazolyl includes isoxazol-3-yl, isoxazol-4-yl and isoxazol-5-yl.

The term oxadiazolyl includes [1,2,4]oxadiazol-3-yl and [1,2,4]oxadiazol-5-yl.

The term pyrazolyl includes pyrazol-3-yl, pyrazol-4-yl and pyrazol-5-yl.

The term thiazolyl includes thiazol-2-yl, thiazol-4-yl and thiazol-5-yl.

The term thiadiazolyl includes [1,2,4]thiadiazol-3-yl, and [1,2,4]thiadiazol-5-yl.

The term isothiazolyl includes isothiazol-3-yl, isothiazol-4-yl and isothiazol-5-yl.

The term imidazolyl includes imidazol-2-yl, imidazolyl-4-yl and imidazolyl-5-yl.

The term triazolyl includes [1,2,4]triazol-3-yl and [1,2,4]triazol-5-yl.

The term tetrazolyl includes tetrazol-5-yl.

The term pyridyl includes pyrid-2-yl, pyrid-3-yl and pyrid-4-yl.

The term pyridazinyl includes pyridazin-3-yl, pyridazin-4-yl, pyridazin-5-yl and pyridazin-6-yl.

The term pyrimidyl includes pyrimidin-2-yl, pyrimidin-4-yl, pyrimidin-5-yl and pyrimidin-6-yl.

The term benzofuryl includes benzofur-2-yl and benzofur-3-yl.

The term benzothienyl includes benzothien-2-yl and benzothien-3-yl.

The term benzimidazolyl includes benzimidazol-2-yl.

The term benzoxazolyl includes benzoxazol-2-yl.

The term benzothiazolyl includes benzothiazol-2-yl.

The term indolyl includes indol-2-yl and indol-3-yl.

The term quinolyl includes quinol-2-yl.

Examples of particular values for $X^1$ are O and CONH.

Examples of particular values for $X^2$ are O, NHCO, CONH, OCO and OCONH, $NR^{10}$ wherein $R^{10}$ represents hydrogen, methyl or, together with $R^1$, pyrrolidinyl, piperidinyl, 4-(N,N-dimethylamino)piperidinyl or N-methylpiperazinyl, NHCO, CONH, OCO and OCONH.

An example of a particular value for $X^3$ is O.

Examples of particular values for $L^a$ are methylene, ethylene, propylene and butylene.

An example of a particular value for $L^b$ is methylene.

An example of a particular value for $L^c$ is methylene.

An example of a particular value for m is 1.

An example of a particular value for n is zero.

Examples of particular values for $R^1$ are hydrogen, methyl, ethyl, propyl, t-butyl, cyclohexyl, phenyl, phenyl substituted with from one to three substituents selected from the group consisting of F, Cl, Br, I, (1–4C)alkyl, (1–4C)alkoxy, trifluoromethyl, CN, $CH_3CONH$, pyridyl, pyrimidyl, N'-pryridonyl, and, together with $X^2$ when it represents $NR^{10}$, pyrrolidinyl, piperidinyl, 4-(N,N-dimethylamino)-piperidinyl or N-methylpiperazinyl.

More particular values of $R^1$ wherein phenyl is substituted with from one to three substituents are as follows:

2-isopropylphenyl, 3-isopropylphenyl, 4-isopropylphenyl, 2-methoxylphenyl, 3-methoxyphenyl, 4-methoxyphenyl, 2-cyanophenyl, 3-cyanophenyl, 4-cyanophenyl, 2-fluorophenyl, 3-fluorophenyl, 4-fluorophenyl, 2-chlorophenyl, 3-chlorophenyl, 4-chlorophenyl, 2-trifluoromethylphenyl, 3-trifluoromethylphenyl, 4-trifluoromethylphenyl, 2-acetamidophenyl, 3-acetamidophenyl, 4-acetamidophenyl, 2,3-difluorophenyl, 3,4-difluorophenyl, 3,5-difluorophenyl, 2,4-difluorophenyl, 2,5-difluorophenyl, 2,3-dichlorophenyl, 3,4-dichlorophenyl, 3,5-dichlorophenyl, 2,4-dichlorophenyl, and 2,5-dichlorophenyl.

Examples of values for $R^2$ are methyl, ethyl, propyl, 2-propyl, butyl, 2-methylpropyl, cyclohexyl, trifluoromethyl, 2,2,2-trifluoroethyl, chloromethyl, ethenyl, prop-2-enyl, methoxyethyl, phenyl, 4-fluorophenyl, or dimethylamino. Preferably $R^2$ is ethyl, 2-propyl or dimethylamino.

Preferably $R^3$ and $R^4$ each represent methyl.

Examples of a (1–6C)alkyl group represented by $R^5$, $R^6$, $R^7$ and $R^8$ are methyl, ethyl and propyl. An example of an aryl(1-C)alkyl group is benzyl. An example of a (2–6C)alkenyl group is prop-2-enyl. An example of a (3–8C) carbocyclic ring is a cyclopropyl ring.

Preferably $R^6$ and $R^7$ each represents hydrogen.

Preferably $R^5$ and $R^8$ each independently represents hydrogen or (1–4C)alkyl, or together with the carbon atom to which they are attached form a (3–8C) carbocyclic ring.

More preferably $R^8$ represents methyl or ethyl and $R^5$ represents hydrogen or methyl, or $R^5$ and $R^8$ together with the carbon atom to which they are attached form a cyclopropyl ring.

Especially preferred are compounds in which $R^8$ represents methyl and $R^5$, $R^6$ and $R^7$ represent hydrogen.

The compounds of formula I may be prepared by (a) reacting a compound of formula

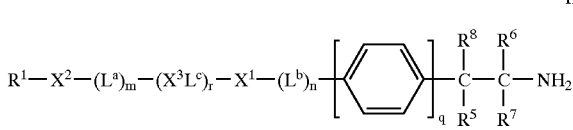

II with a compound of formula

  III in which $Z^1$ represents a leaving atom or group;

(b) for a compound of formula I in which $X^1$ is CONH, reacting a compound of formula

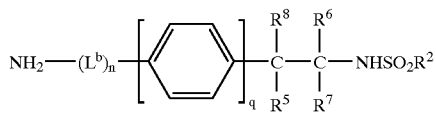

IV with a compound of formula

  V in which $Z^2$ represents a hydroxyl group or a leaving atom or group;

(c) for a compound of formula I in which q is 2, coupling a compound of formula

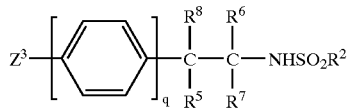

VI in which q is 1 and $Z^3$ represents a halogen atom, with a compound of formula

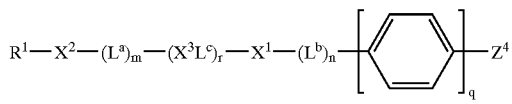

VII in which q is 1 and $Z^4$ represents a halogen atom;

(d) reacting a compound of formula

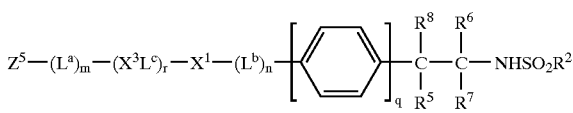

VIII in which $Z^5$ represents a leaving atom or group, with a compound of formula

  IX or (e) reacting a compound of formula

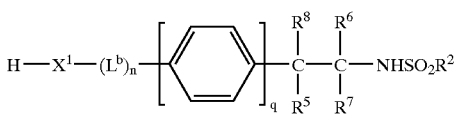

X or a protected derivative thereof, with a compound of formula

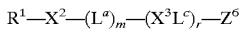  XI in which $Z^6$ represents a leaving atom or group; followed where necessary and/or desired by forming a pharmaceutically acceptable salt.

In step (a) of the process, the leaving atom or group represented by $Z^1$ may be, for example, a halogen atom such as a chlorine or bromine atom. The reaction is conveniently performed in the presence of a base, for example an alkali metal hydroxide such as sodium hydroxide, an alkali metal carbonate such as potassium carbonate, a tertiary amine such as triethylamine or 1,8-diazabicyclo[5.4.0]undec-7-ene. Suitable solvents include halogenated hydrocarbons such as dichloromethane. The reaction is conveniently performed at a temperature in the range of from −20 to 100° C., preferably from −5 to 50° C.

In step (b) of the process, the leaving atom or group represented by $Z^2$ may be, for example, a halogen atom such as a chlorine or bromine atom. It is conveniently generated in situ, for example by reaction of a compound of formula V in which $Z^2$ represents a hydroxyl group with a halogenating agent, such as oxalyl chloride, or with a dehydrating agent, such as a carbodiimide, for example 1-[3-dimethylaminopropyl]-3-ethyl carbodiimide hydrochloride.

The reaction is conveniently performed in the presence of a base, for example an alkali metal hydroxide such as sodium hydroxide, an alkali metal carbonate such as potassium carbonate, or a tertiary amine such as triethylamine, 4-dimethylaminopyridine or 1,8-diazabicyclo[5.4.0]undec-7-ene.

Suitable solvents include halogenated hydrocarbons such as dichloromethane.

The reaction is conveniently performed at a temperature in the range of from −20 to 100° C., preferably from −5 to 50° C.

In step (c) of the process, $Z^3$ and $Z^4$ may each represent, for example, a bromine atom. The process is conveniently performed by reacting the compound of formula VII with a strong base, such as an organolithium, for example butyl lithium, followed by a trialkyl boronic acid, such as trimethylboronic acid. The reactions are conveniently performed in the presence of a solvent, such as an ether, for example tetrahydrofuran. The temperature is conveniently maintained in the range of from −78 to 0° C. The resultant boronic acid derivative is then reacted with the compound of formula VI in the presence of a tetrakis (triarylphosphine) palladium(0) catalyst, such as tetrakis (triphenylphosphine) palladium(0), an alcohol, such as n-propyl alcohol and a base such as potassium carbonate. Convenient solvents for the reaction include ethers such as ethylene glycol dimethyl ether (DME). The temperature at which the reaction is conducted is conveniently in the range of from 0 to 150° C., preferably 75 to 120° C.

In step (d) of the process, the leaving atom or group represented by $Z^5$ may be, for example, a halogen atom such as a chlorine atom. Where the compound of formula IX is not basic, the reaction is conveniently performed in the presence of a base, for example a tertiary amine, such as triethylamine or an alkali metal hydride, such as sodium hydride. If desired, the reaction may be performed in the presence of a catalytic amount of an alkali metal iodide, such as potassium iodide. Suitable solvents include aromatic hydrocarbons, such as toluene and amides, such as dimethylformamide. The temperature is conveniently in the range of from 0 to 120° C.

In step (e) of the process, the leaving atom or group represented by $Z^6$ may be, for example, a halogen atom such as a chlorine atom. The protected derivative may, for example, be protected on nitrogen by a nitrogen protecting group, such as N-t-butoxycarbonyl. Where the compound of formula XI is not basic, the reaction is conveniently performed in the presence of a base, for example an alkali metal hydride, such as sodium hydride. If desired, the reaction may be performed in the presence of a catalytic amount of an alkali metal iodide, such as potassium iodide. Suitable solvents include amides, such as dimethylformamide. The temperature is conveniently in the range of from 0 to 120° C.

For the preparation of compounds of formula I in which $X^2$ represents NHCO, it may be convenient to prepare a corresponding N-protected (e.g. N-t-butoxycarbonyl protected) compound of formula I in which $R^1X^2$ represents a protected carboxyl group (for example a (1–6C)alkyl ester) by process (e), using as staring material a compound of formula XI in which $R^1X^2$ is a protected carboxyl group; deprotect the protected carboxyl group (for example by hydrolysis using aqueous lithium hydroxide); react this with an amine of formula $R^1NH_2$, and then deprotect the resultant amide, for example by removing an N-t-butoxycarbonyl protecting group with trifluoroacetic acid.

The compounds of formula II are known or may be prepared by conventional methods, for example by reducing a corresponding amide or nitrile using borane.

The compounds of formula IV in which n is zero may be prepared by reducing the nitro group in a corresponding nitrophenyl compound, for example by catalytic hydrogenation in the presence of a Group VIII metal catalyst such as palladium on charcoal. The compounds where n is 1 may be prepared by reducing a corresponding nitrile or amide.

The compounds of formula VI may be prepared by reacting a compound of formula

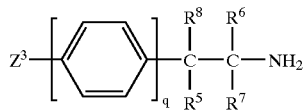

XII with a compound of formula III using a method analogous to that of process (a) above.

The compounds of formula X may be prepared by reacting a compound of formula

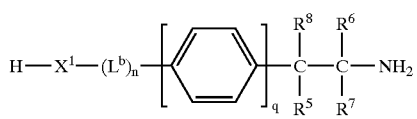

XIII or a derivative thereof substituted on $X^1$ with a protecting group, for example a benzyl group, with a compound of formula III, according to the method of step (a) above. A benzyl protecting group may be removed, for example, by reaction with ammonium formate in the presence of palladium on carbon. A t-butoxycarbonyl nitrogen protecting group may be introduced, for example, by reaction of an unprotected compound with di-tert-butyl dicarbonate, conveniently in the presence of a base such as 4-dimethylaminopyridine. Suitable solvents include halogenated hydrocarbons, such as dichloromethane.

The compounds of formula XII and XIII are known or may be prepared by conventional methods, for example by reducing a corresponding amide or nitrile using borane.

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into $GluR^4$ transfected HEK293 cells, as described in more detail below.

In one test, 96 well plates containing confluent monolayers of HEK cells stably expressing human GluR4B (obtained as described in European Patent Application Publication Number EP-A1-583917) are prepared. The tissue culture medium in the wells is then discarded, and the wells are each washed once with 200 µl of buffer (glucose, 10 mM, sodium chloride, 138 mM, magnesium chloride, 1 mM, potassium chloride, 5 mM, calcium chloride, 5 mM, N-[2-hydroxyethyl]piperazine-N-[2-ethanesulfonic acid], 10 mM, to pH 7.1 to 7.3). The plates are then incubated for 60 minutes in the dark with 20 µM Fluo3-AM dye (obtained from Molecular Probes Inc, Eugene, Oreg.) in buffer in each well. After the incubation, each well is washed once with 100 µl buffer, 200 µl of buffer is added and the plates are incubated for 30 minutes.

Solutions for use in the test are also prepared as follows. 30 µM, 10 µM, 3 µM and 1 µM dilutions of test compound are prepared using buffer from a 10 mM solution of test compound in DMSO. 100 µM cyclothiazide solution is prepared by adding 3 µl of 100 mM cyclothiazide to 3 ml of buffer. Control buffer solution is prepared by adding 1.5 µl DMSO to 498.5 µl of buffer.

Each test is then performed as follows. 200 µl of control buffer in each well is discarded and replaced with 45 µl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 µl of buffer and 45 µl of test compound in buffer in appropriate wells. A second fluorescent reading is taken after 5 minutes incubation. 15 µl of 400 µM glutamate solution is then added to each well (final glutamate concentration 100 µM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 µM cyclothiazide.

In another test, HEK293 cells stably expressing human $GluR^4$ (obtained as described in European Patent Application Publication No. EP-A1-0583917) are used in the electro-physiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm $kg^{-1}$. The intracellular recording solution contains (in mM): 140 CsCl, 1 $MgCl_2$, 10 HEPES, (N-[2-hydroxyethyl]piperazine-$N^1$-[2-ethanesulfonic acid]) 10 EGTA (ethylene-bis (oxyethylenenitrilo)tetraacetic acid), pH=7.2 with CsOH, 295 mOsm $kg^{-1}$. With these solutions, recording pipettes have a resistance of 2–3 MΩ. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM, they produce a greater than 30% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

|  | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
Tablets each containing 60 mg of active ingredient are made as follows:

| Active Ingredient | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein the term "effective amount" refers to the amount or dose of the compound which provides the desired effect in the patient under diagnosis or treatment.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following examples and preparations are understood to be illustrative only and are not intended to limit the scope of the present invention in any way. The reagents and starting materials are readily available to one of ordinary skill in the art. As used herein, the following terms have the indicated meanings: "kg" refers to kilograms; "g" refers to grams; "mg" refers to milligrams; "μg" refers to micrograms; "mmol" or "mMol" refers to millimoles; "L" refers to liters; "mL" refers to milliliters; "μL" refers to microliters; "cm" refers to centimeters; "M" refers to molar; "eq" refers to equivalents; "N" refers to normal; "ppm" refers to parts per million; "δ" refers to parts per million down field from tetramethylsilane; "° C." refers to degrees Celsius; "mm Hg" refers to millimeters of mercury; "kPa" refers to kilopascals; "psi" refers to pounds per square inch; "bp" refers to boiling point; "mp" refers to melting point; "dec" refers to decomposition; "h" or "hr" refers to hours; "min" refers to minutes; "sec" refers to seconds; "THF" refers to tetrahydrofuran; "DMF" refers to N,N-dimethylformamide; "DMSO" refers to dimethyl sulfoxide; "EDCI HCl" refers to 1-ethyl-3-[3-(dimethylamino)propyl]carbodiimide hydrochloride; "EtoAc" refers to ethyl acetate; "EtOH" refers to ethanol; "MeOH" refers to methanol; and "LAH" refers to lithium aluminum hydride.

PREPARATION 1

2-(4-Nitrophenyl)propionitrile

A −15° C. solution of 4-nitroacetophenone (16.5 g, 100 mmol) and tosylmethyl isocyanide (2.9.3 g, 150 mmol) in methoxyethyl ether (400 mL) was slowly treated with a room temperature solution of the potassium t-butbxide. (28 g, 250 mmol) in t-butanol (200 mL). The reaction mixture was stirred at −15° C. for 1 h and then allowed to warm to room temperature over night. Water (100 mL) was added to the mixture and the organic layer was extracted with ether (3×200 mL). The combined organic fraction was washed with water (3×200 mL), brine (100 mL), dried over sodium sulfate, and concentrated in vacuo to give the crude material which was further purified by flash chromatography ($SiO_2$, 30% EtOAc: Hexane) to give 13.6 g (77%) of the title compound. The NMR spectrum was consistent with the proposed title structure. Field Desorption Mass Spectrum: $M^+$=176.

PREPARATION 2

2-(4-Nitrophenyl)propylamine

A 0° C. solution of the material from Preparation 1 (11.8 g, 67 mmol) in dry THF (200 mL) was treated with borane tetrahydrofuran (1 M in THF, 72 mL, 72 mmol). The reaction mixture was stirred at room temperature for 16 h. A solution of THF:MeOH (1:1, 10 mL)and sodium hydroxide (5 N, 40 mL) were added to the reaction mixture stepwise and the mixture was refluxed for 5 h. The reaction mixture was allowed to cool to ambient temperature. The reaction mixture was extracted with dichloromethane (3×100 mL). The combined organic fraction was washed with water (3×200 mL), brine (100 mL), dried over potassium carbonate, and concentrated in vacua to give the crude material which was further purified by flash chromatography ($SiO_2$, 5% MeOH: $CH_2Cl_2$) to give 8.5 g (71%) of the pure product. The NMR spectrum was consistent with the proposed title structure. Field Desorption Mass Spectrum:M'= 181.

PREPARATION 3

N-2-(4-Nitrophenyl)propyl 2-Propanesulfonamide

A 0° C. suspension of the material from Preparation 2 (8.2 g, 45.3 mmol) in dichloromethane (200 mL) was treated with 1,8-diazabicyclo[5.4.0]undec-ene (7.6 g, 49.8 mmol) followed by 2-propylsulfonyl chloride (12 g, 49.8 mmol). The reaction mixture was stirred at 0° C. for 1 h and at room temperature for an extra 12 h. The reaction was stopped by the addition of water (100 mL). The organic layer was extracted with dichloromethane (3×200 mL). The combined organic fraction was washed with water (3×200 mL), brine (100 mL), dried over potassium carbonate, and concentrated in vacuo to give the crude material which was further purified by flash chromatography ($SiO_2$, 30% EtOAc: Hexane) to give 8.9 g (68%) of the pure product. The NMR spectrum was consistent with the proposed title structure. Field Desorption Mass Spectrum:$M^+$=287.

PREPARATION 4

N-2-(4-Aminophenyl)propyl 2-Propanesulfonamide

A degassed solution of the material from Preparation 3 (8.75 g, 31 mmol) in ethyl acetate (200 mL) was treated with palladium on carbon (4 g, 50 mol %). The mixture was shaken under 60 psi of hydrogen gas for 2 h. The reaction mixture was filtered through a celite cake and the filtrate was concentrated in vacuo to yield 7.44 g (94%) of the pure product. The NMR spectrum was consistent with the proposed title structure. Field Desorption Mass Spectrum:$M^+$= 257.

PREPARATION 5

N-2-[4-(Chloroacetamido)phenyl]propyl 2-Propanesulfonamide

The product of Preparation 4 (2.0 g, 7.8 mMol) and sodium carbonate (910 mg, 1.1 eq.) were placed into acetone (60 mL) and stirred at ambient temperature under nitrogen. To this mixture, chloroacetyl chloride (971 mg, 1.1 Eq.) in acetone (10 mL) was added dropwise over a 10 minute period. After 1 hour stirring at ambient temperature, the solution was filtered through celite and concentrated under reduced pressure to yield a white solid (3.0 g). Purification was achieved by silica gel chromatography using the prep. 2000 instrument and eluting with a gradient solvent of methylene chloride to methylene chloride/ethyl acetate 9:1 over a 30 minute period to yield the title compound (2.16 g) as white crystals. m.p. 137.5°–138.5° C. The NMR spectrum was consistent with the proposed structure. Ion spray mass spectrum: M+1=333.2 Analysis calculated for $C_{14}H_{21}N_2O_3ClS$: % C, 50.52; % H, 6.36; % N, 8.42. Found: % C, 50.81; % H, 6.42; % N, 8.43.

PREPARATION 6

4-(N,N-Dimethylaminopropyloxy)phenyl Bromide 4-bromophenol (5.0 g, 28.9 mmol) and 2-dimethylaminoethyl chloride hydrochloride (4.6 g, 31.8 mmol) were combined in a mixture of toluene (100 mL) and 1 M NaOH (50 mL) and heated at reflux for 16 h. The layers were separated and the organic phase was washed with 1 M NaOH, dried ($MgSO_4$) and concentrated to yield 4.2 g of the title compound as a yellow oil which was used without further purification. $^1$H NMR (400 MHz, $CDCl_3$): δ 2.34 (6H, s), 2.72 (2H, t), 4. 01 (2H, t), 6.73 (2H, m), 7.33 (2H, m).

PREPARATION 7

2-(4-Bromophenyl)propylamine Hydrochloride

To a −15° C. solution of 50.0 g (251.2 mmol) of 4-bromoacetophenone and 49.0 g (251.2 mmol) of tosylmethyl isocyanide in 800 mL of dry dimethoxyethane was added a hot solution of 50.7 g (452.2 mmol) of potassium tert-butoxide in 230 mL of tert-butyl alcohol dropwise at a rate to maintain the temperature below 0° C. The reaction was stirred at −5° C. for 45 min after addition was complete. The cooling bath was removed and the reaction stirred for 2.5 h more. The mixture was concentrated in vacuo to a volume of 200 mL and diluted with 500 mL of water. The aqueous mixture was extracted four times with diethyl ether, and the combined organic portions were dried ($MgSO_4$), filtered and concentrated in vacuo. The residue was dissolved in 55 mL of tetrahydro-furan and heated to reflux. To the refluxing solution was added slowly dropwise 27.6 mL 276.3 mmol) of 10.0 M borane-dimethylsulfide complex. Refluxing was continued for 20 min after addition was complete. The mixture was cooled to ambient temperature and methanol saturated with hydrogen chloride was added very slowly until pH 2 was achieved. The mixture was concentrated in vacuo and the residue was dissolved in methanol and concentrated in vacuo again. The solid residue was suspended in 125 mL of ethanol, filtered, rinsed with ethanol then diethyl ether. The white solid was dried in vacuo to afford 25.4 g (40%) of the title compound. The filtrate was concentrated in vacuo and suspended in diethyl ether. The solid was filtered, rinsed with diethyl ether and dried in vacuo to afford another 15.6 g (25%) of the title compound.

PREPARATION 8

N-2-(4-Bromophenyl)propyl 2-Ppropylsulfonamide

To a suspension of 0.5 g (2.0 mmol) of the product of Preparation 7 in 5 mL of dichloromethane was added 0.6 mL (4.0 mmol) of triethylamine. The mixture was cooled to 0° C. and 0.2 mL (2.0 mmol) of isopropylsulfonyl chloride was added. After stirring at 0° C. for 20 min, the mixture was washed once with 10% aqueous sodium bisulfate and the organic layer was separated. The aqueous layer was extracted three times with dichloromethane. The combined organic portions were dried ($Na_2SO_4$), filtered and concentrated in vacuo. Chromatography on 50 g silica gel (35% ethyl acetate/hexane) afforded 0.2 g (25%) of the title compound. Analysis calculated for $C_{12}H_{18}NO_2SBr$: %C, 45.01; %H, 5.67; %N, 4.37. Found: %C, 45.30; %H, 5.92; %N, 4.43. Field Desorption Mass Spectrum: M+1=321.

PREPARATION 9

2-(4-Benzyloxyphenyl)propionitrile

To a −15° C. solution of 4-benzyloxyacetophenone (500 mg, 2.2 mmol)and tosylmethyl isocyanide (650 mg, 3.3 mmol) in 10 mL of dry dimethoxyethane was added 2 mL of a warm solution of potassium tert-butoxide (500 mg, 4.5 mmol) in tert-butyl alcohol dropwise at a rate to maintain the temperature below 0° C. The reaction was stirred at −5° C. for 45 min after addition was complete. The cooling bath was removed and the reaction stirred for 2.5 h more. The mixture was concentrated in vacuo to a volume of 2 mL and diluted with 10 mL of water. The organic layer was extracted four times with ethyl acetate, and the combined organic portions were dried ($MgSO_4$), filtered and concentrated in vacuo. The crude product was purified by flash chromatography ($SiO_2$, EtOAc/Hexanes; 0–25%, gradient) to yield 0.370 g (71%) of the title compound. Electrospray Mass Spectrum: 237.1 Analysis calculated for $C_{16}H_{15}NO$: C; 81.00, H; 6.30, N; 5.90. Found: C; 81.04, H; 6.64, N; 6.17.

PREPARATION 10

2-(4-Benzyloxyphenyl)propylamine Hydrochloride

To an ambient solution of the product of Preparation 9 (1.6 g, 6.75 mmol) in 10 mL of tetrahydrofuran was added borane dimethylsulfide (0.75 mL of the 10 M solution, 7.5 mmol). The reaction mixture was refluxed for 1 h. The mixture was cooled to ambient temperature and the solvent was removed in vacuum. The crude product was dissolved in ether and this mixture was treated with a saturated solution of HCl in methanol (3×20 mL). The resulting white product was precipitated out of ether and collected by filtration to give 1.6 g (86%) of the title compound. Electospray Mass Spectrum: 242 (M−HCl).

PREPARATION 11

N-2-(4-Benzyloxyphenyl)propyl) 2-Propanesulfonamide

The title compound was prepared from the product of Preparation 10 and 2-propylsulfonyl chloride as described in Preparation 3. Electrospray Mass Spectrum: M=347.2. Analysis calculated for $C_{19}H_{25}NO_3S$: %C, 65.68; %H, 7.25; %N, 4.03. Found: %C, 65.63; %H, 7.31; %N, 4.07.

PREPARATION 12

N-t-Butoxycarbonyl-N-(2-(4-hydroxyphenyl)propyl) 2-Propanesulfonamide

The product of Preparation 11 (7.6 g, 23.8 mmol) was dissolved in dichloromethane (100 ml) and to this mixture was added di-tert-butyl dicarbonate (5.71 g, 26.2 mmol) and 4-dimethylaminopyridine (1.45 g, 11.9 mmol). The reaction was stirred at ambient temperature for 1 hour. The reaction mixture was washed with a saturated aqueous solution of sodium hydrogen sulfate and brine. The organic fraction was dried over magnesium sulfate and concentrated under vacuo. The protected sulfonamide (9.00 g, 21.0 mmol) was dissolved in ethyl acetate: $H_2O$ (5:1) and ammonium formate (2.0 g, 31.5 mmol) added to the mixture. Then palladium on carbon (10%) (0.9 g) was added to the reaction and this was stirred at ambient temperature for 6 hours. The suspension was filtered through celite and the resulting solution concentrated in vacuo to give 5.51 g (78%) of the title product. Electrospray Mass Spectrum: M=356.2. Analysis calculated for $C_{15}H_{23}NO_5S$: %C, 57.12; %H, 7.61; %N, 3.92. Found: %C, 57.41; %H, 7.66; %N, 3.83.

PREPARATION 13

N-2-[4-(2-Chloroethyl)oxyphenyl]propyl 2-Propanesulfonamide

The product of Preparation 12 (4 g, 11.2 mmol) was dissolved in acetone and potassium carbonate (4.64 g, 33.6 mmol) was added. After 30 minutes 1-bromo-2-chloroethane (1.12 mL, 13.44 mmol) was added to the reaction and the mixture was heated under reflux while stirring for 24 hours. The reaction mixture was partitioned between ethyl acetate and water. The organic layer was washed with brine, dried over sodium sulfate and concentrated in vacuo. Chromatography ($SiO_2$, 10% ethyl acetate/hexane) gave 1.5 g (32%) of the pure product. Electrospray Mass Spectrum:

419.2. Analysis calculated for $C_{19}H_{30}ClNO_5S \cdot H_2O$: % C, 53.20; %H, 7.28; %N, 3.26. Found: %C, 53.10; %H, 6.27; %N, 3.59.

PREPARATION 14

N-Tertbutoxyacetyl-2-(4-(2-chloroethoxy)-phenyl)-propyl-2-propanesulfonamide

To a stirred mixture of N-tertbutoxyacetyl-2-(4-hydroxyphenyl)propyl-2-propanesulfonamide (4.0 g, 11.2 mmol) in acetone (40 mL) was added potassium carbonate (4.64 g, 33.6 mmol) under nitrogen. The resulting mixture was stirred 30 minutes at ambient temperature. Next, 1-bromo-2-chloroethane (1.12 ml, 13.4 mmol) was added and the resulting mixture was heated to reflux while stirring for 48 h. The resulting mixture was cooled and partitioned between ethyl acetate and water. The organic layer was washed with water (2×50 mL) and brine (1×50 mL), dried over magnesium sulfate, and filtered. Evaporation of the filtrate in vacuo followed by chromatography on silica gel eluting with ethyl acetate-hexane gave 1.5 g (32%) of the pure title compound.

Field Desorption Mass Spectrum: M=419.2; Analysis for $C_{19}H_{30}ClNO_5S$: Theory: C, 54.34; H, 7.20; N, 3.34. Found: C, 54.24; H, 7.36; N, 3.33.

PREPARATION 15

N-(4-Fluorobenzyl)-chloroacetamide

To a stirred mixture of 4-fluorobenzylamine (685 uL, 6.0 mmol) and dry tetrahydrofuran (20 mL) was added triethylamine (1.25 mL, 9.0 mmol) under nitrogen. The resulting mixture was stirred for 10 minutes at ambient temperature. Next, chloroacetyl chloride (477 uL, 6.0 mmol) was added and the resulting mixture was stirred for 1 h. at ambient temperature. The resulting mixture was partitioned between ethyl acetate and water. The organic layer was washed with water (2×20 mL) and brine (1×20 mL), dried over magnesium sulfate, and filtered. Evaporation of the filtrate in vacuo followed by chromatography on silica gel eluting with ethyl acetate-hexane gave 1.09 g (91%) of the pure title compound.

Mass Spectrum: $MS^{-1}$=200.1; Analysis for $C_9H_9ClFNO$: Theory: C, 53.61; H, 4.50; N, 6.95. Found: C, 53.39; H, 4.52; N, 7.01.

PREPARATION 16

N-t-Butoxycarbonyl-N-(2-(4-(methoxyacetyl)oxy) phenyl)propyl) 2-Propanesulfonamide A solution of phenol from Preparation 12 (10 g, 28 mmol) in dry dimethylformamide (70 ml) was treated gradually with sodium hydride (1.35 g, 33.6 mmol). The mixture was stirred for 1 hour at room temperature and then was treated with methyl bromoacetate (5.14 g, 33.6 mmol). The reaction mixture was stirred at 60° C. for 6 hours. The resulting mixture was cooled and partitioned between ethyl acetate and water. The organic layer was washed with water (2×100 ml) and brine (1×100 ml), dried over sodium sulfate, and filtered. Evaporation of the filtrate in vacuo followed by chromatography on silica gel eluting with ethyl acetate-hexane (10% to 30%) gave 7 g (58%) of the title compound.

Electrospray Mass Spectrum: 429; Analysis for $C_{20}H_{31}NO_7S \cdot HBr$: Theory: C, 53.41; H, 7.00; N, 3.11. Found C, 53.25; H, 6.66; N, 3.71.

PREPARATION 17

N-t-Butoxycarbonyl-N-(2-(4-(hydroxyacetyl)oxy) phenyl)propyl) 2-Propanesulfonamide A solution of phenol from Preparation 16 (6.7 g, 15.6 mmol) in THF:MeOH:$H_2O$ (78 ml of 3:2:1) was treated with lithium hydroxide (0.94 g, 23.4 mmol). The mixture was stirred for 12 hour at room temperature. The resulting mixture was partitioned between ethyl acetate and aqueous HCl (10%). The organic layer was washed with water (2×50 mL) and brine (1×50 mL), dried over sodium sulfate, and filtered. Evaporation of the filtrate in vacuo gave 5.7 g (88%) of the title compound.

PREPARATION 18

Pip-Pip HOBT

A solution of 4-chloro-3-nitrobenzyl sulfonylchloride (7.68 g, 30 mmol) in dry dichlorometane (120 mL) was added dropwise to a solution of triethylamine (5 mL, 36 mmol) and 4-piperidinopiperidine (5.04 g, 30 mmol) in dichloromethane (30 ml). The mixture was stirred for 3 hour at room temperature. The resulting mixture was partitioned between dichloromethane and aqueous sodium hydrogensulfate (10%). The organic layer was washed with sodium hydrogensulfate solution (2×100 mL) and brine (1×100 mL), dried over sodium sulfate, and filtered. Evaporation of the filtrate in vacuo gave quantitative yield of the orange solid which was added to a 95:5 mixture of EtOH:MeOH (200 mL). This mixture was treated with hydrazine hydrate (60 mL).

The resulting mixture was refluxed for 3 hours. The unreacted hydrazine and water were removed under reduced pressure. EtOH (50 mL) was added to the resulting product and the solvent was removed in vacuo. To the resulting product was added water (250 mL) and the mixture was stirred in ice bath for 2 hours, then chilled in the refrigerator for 1 hour. The resulting mixture was filtered to give 5.94 g of the title compound.

EXAMPLE 1

N-2-[4-((3-N,N-Dimethylaminopropyl)-carboxamido)phenyl]propyl 2-Propanesulfonamide

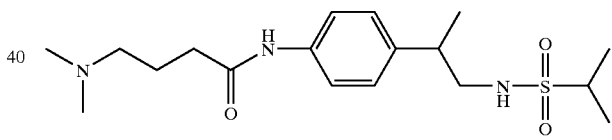

To an ambient temperature solution of 4-(N,N-dimethylamino)butyric acid (0.167 g, 1.0 mmol) in methylene chloride (10 mL) was added oxalyl chloride (0.254 g, 2 mmol) portionwise. Initiation of the reaction was accomplished by the addition of one drop of dimethylformamide. The reaction mixture was stirred for 2 hours at ambient temperature. The reaction mixture was then concentrated under vacuum to give an oily product which was subsequently treated with triethylamine (0.200 g, 2 mmol) and the product of Preparation 4 (0.256 g, 1 mmol) in methylene chloride (50 mL). The reaction mixture was stirred at ambient temperature for 16 hours. The solution was then concentrated under vacuum to yield an oil (0.314 g). Purification of the oil by chromatotron silica gel chromatography using a 2000 micron rotor and eluting with a gradient solvent of ethyl acetate/methanol 1:1 and 1% ammonium hydroxide to methanol/1% ammonium hydroxide afforded the title compound (78 mg) as a clear oil. The NMR spectrum was consistent with the proposed structure. Ion spray mass spectrum M+1=370.4 Analysis calculated for $C_{18}H_{31}N_3O_3S \cdot 0.75H_2O$: %C, 56.44; %H, 8.55; N, 10.97. Found: %C, 56.47; %H, 8.49; %N, 10.98.

EXAMPLE 2

N-2-[4-(N,N-Dimethylglycinamido)phenyl]propyl 2-Propanesulfonamide Maleate

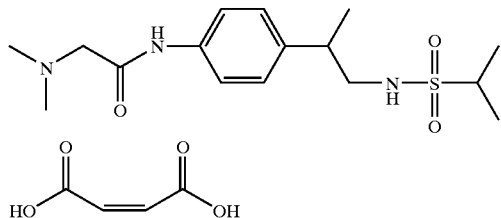

N,N-Dimethylglycine (0.103 g, 1.0 mMol), oxalyl chloride (1.3 g, 10 mmol), triethylamine (1.01 g, 10 mmol), and the product of Preparation 4 (0.200 g, 0.78 mmol) in methylene chloride (50 mL) were reacted as described in Example 1 to yield an oil (0.187 g). The oil was purified by chromatotron silica gel chromatography using a 1000 micron rotor and eluting with an isocratic solvent of ethyl acetate to yield a clear oil (0.30 g). The NMR spectrum was consistent with the proposed structure. Field absorption mass spectrum: M=340 This material was reacted with maleic acid to give the title compound (0.036 g) as a white solid. m.p. 120°–122° C. Analysis calculated for $C_{20}H_{31}N_3O_7S$-$0.5H_2O$: %C, 51.50; %H, 6.65; %N, 9.01. Found: %C, 51.39; %H, 6.47; %N, 8.89.

EXAMPLE 3

N-2-[4-(Aminocarbonylmethoxyacetamido)phenyl]propyl 2-Propanesulfonamide

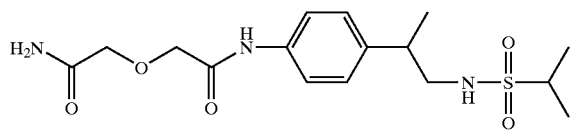

The product of Preparation 4 (0.300 g, 1.17 mmol), aminocarbonylmethoxyacetic acid (0.156 g, 1.17 mmol), 4-dimethylaminopyridine (0.036 g, 0.29 mmol), 1-[3-dimethylamino-propyl]-3-ethyl carbodiimide hydrochloride (0.449 mg, 2.34 mmol), and triethylamine (1.0 g, 9.9 mmol) were placed in methylene chloride (25 mL) and stirred overnight under nitrogen at ambient temperature. In the morning, the reaction was diluted with an additional 25 mL methylene chloride and the organic solution was washed once with water, dried over $K_2CO_3$, and concentrated under reduced pressure to yield 1.8 g. of a semi-solid. Purification was achieved by chromatotron silica gel chromatography using a 4000 micron rotor and eluting with an isocratic solvent of ethyl acetate/methanol 9:1 to yield the title compound (0.080 g) as a clear liquid. The NMR spectrum was consistent with the proposed structure. Ion spray mass spectrum: M+1=372.2 IR shows amide carbonyl stretch at 1690.88 $cm^{-1}$. Analysis calculated for $C_{16}H_{25}N_3O_5S$: %C, 51.74; %H, 6.78; %N, 11.31. Found: %C, 51.36; %H, 6.78; %N, 11.00.

EXAMPLE 4

N-2-[4-(3-Methoxycarbonylpropanoyl)amido)-phenyl]propyl 2-Propanesulfonamide

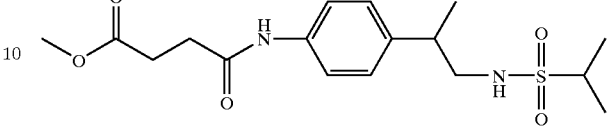

The product of Preparation 4 (0.256 g, 1.0 mmol), monomethyl succinate (0.132 g, 1.0 mmol), 4-dimethylamino pyridine (.015 mg, 0.12 mmol), 1-[3-dimethylamino-propyl]-3-ethyl carbodiimide hydrochloride (0.384 g, 2.0 mmol), and triethylamine (0.025 g, 0.25 mmol) were placed in methylene chloride (25 mL) and reacted as described in Example 3 to yield a semi-solid (1.41 g). Purification was achieved by chromatotron silica gel chromatography using a 2000 micron rotor and eluting with an isocratic solvent of methylene chloride/methanol 19:1 to yield the title compound (0.160 g). as a semi-solid. The NMR spectrum was consistent with the proposed structure. Ion spray mass spectrum: M+1=371.2 Analysis calculated for $C_{17}H_{26}N_2O_5S$: %C, 55.12; %H, 7.07; %N, 7.56; Found: %C, 55.31; %H, 7.20; %N, 7.49.

EXAMPLE 5

N-2-[4-(4-Acetamido)butanoylamido)phenyl]-propyl 2-Propanesulfonamide

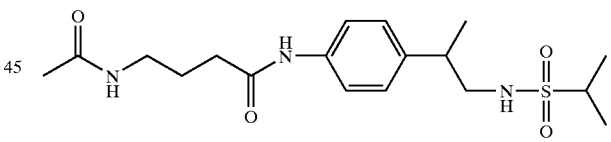

The product of Preparation 4 (0.256 g, 1.0 mmol, 4-acetamidobutyric acid (0.145 g, 1.0 mmol), 4-dimethylaminopyridine (0.015 g, 0.12 mmol), 1-[3-dimethylaminopropyl]-3-ethyl carbodiimide hydrochloride (0.384 g, 2.0 mMol), and triethylamine (0.025 mg, 0.25 mmol) were placed in methylene chloride (25 mL) and reacted as described in Example 3 to yield an oil (1.62 g). Purification was achieved by chromatotron silica gel chromatography using a 2000 micron rotor and eluting with an isocratic solvent of ethyl acetate/methanol 19:1 to yield the title compound (0.118 g) as a clear oil. NMR was consistent with the proposed structure. Ion spray mass spectrum: M+1=384.2 Analysis calculated for $C_{18}H_{29}N_3O_4S$: %C, 56.32; %H, 7.56; %N, 10.95. Found: %C, 56.64; %H, 7.62; %N, 11.30.

EXAMPLE 6

N-2-[4-(4-(t-Butoxycarbonylamino)butanoylamido)phenyl]propyl 2-Propanesulfonamide

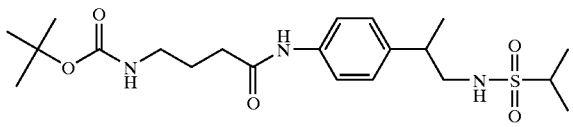

The product of Preparation 4 (0.256 g, 1.0 mmol, 4-t-butoxycarbonylaminobutyric acid(0.203 g, 1.0 mmol), 4-dimethylaminopyridine (0.15 g, 0.12 mmol), 1-[3-dimethylaminopropyl]-3-ethyl carbodiimide hydrochloride (0.384 g, 2.0 mmol), and triethylamine (0.025 g, 0.25 mmol) were placed in methylene chloride (25 mL) and reacted as described in Example 3 to yield an oil (1.55 g). Purification was achieved by chromatotron silica gel chromatography using a 2000 micron rotor and eluting with an isocratic solvent of methylene chloride/methanol 19:1 to yield the title compound (0.317 g) as a clear oil. The NMR spectrum was consistent with the proposed structure. Ion spray mass spectrum: M+1=442.2.

EXAMPLE 7

N-2-[4-(3-Piperidinylpropanoylamido)-phenyl]propyl 2-Propanesulfonamide

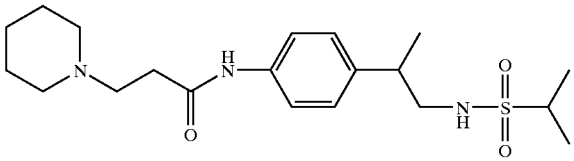

The product of Preparation 4 (0.256 g, 1.0 mmol), 3-piperidinylpropionic acid (0.157 g, 1.0 mmol), 4-dimethylaminopyridine (0.015 g, 0.12 mmol), 1-[3-dimethylamino-propyl]-3-ethyl carbodiimide hydrochloride (0.384 g, 2.0 mmol), and triethylamine (0.025 g, 0.25 mmol) were placed in methylene chloride (25 mL) and reacted as described in Example 3 to yield an oil (1.84 g). Purification was achieved by chromatotron silica gel chromatography using a 2000 micron rotor and eluting with an isocratic solvent of ethyl acetate/methanol 9:1 to yield the title compound (0.280 g) as a clear oil. The NMR spectrum was consistent with the proposed structure. Ion spray mass spectrum: M+1=396.2 Analysis calculated for $C_{20}H_{33}N_3O_3S$-0.25$H_2O$: %C, 59.92: %H, 8.20; %N, 10.48. Found: %C, 59.97; %H, 8.78; %N, 10.02.

EXAMPLE 8

N-2-[4-(5-N,N-Dimethylamino)pentanoylamido)phenyl]propyl 2-Propanesulfonamide

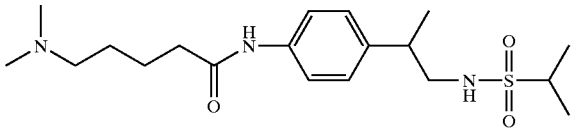

The product of Preparation 4 (0.256 g, 1.0 mmol), 5-N,N-dimethylaminovaleric acid (0.181 mg, 1.0 mmol), 4-dimethylaminopyridine (0.015 mg, 0.12 mmol), 1-[3-dimethylamino-propyl]-3-ethyl carbodiimide hydrochloride (0.384 g, 2.0 mmol), and triethylamine (0.050 g, 0.50 mmol) were placed in methylene chloride (25 mL) and reacted as described in Example 3 to yield an oil (1.77 g). Purification was achieved by chromatotron silica gel chromatography using a 2000 micron rotor and eluting with an isocratic solvent of methylene chloride/methanol 9:1 to yield the title compound (0.289 g) as a clear oil. The NMR spectrum was consistent with the proposed structure. Ion spray mass spectrum: M+1=384.2 Analysis calculated for $C_{19}H_{33}N_3O_3S$-0.5$H_2O$ %C, 58.09; %H, 8.67; %N, 10.95. Found: %C, 58.11; %H, 8.67; %N, 11.04.

EXAMPLE 9

N-2-[4-(3-N-Cyclohexylamino)-propanoylamido)phenyl]propyl 2-Propanesulfanamide

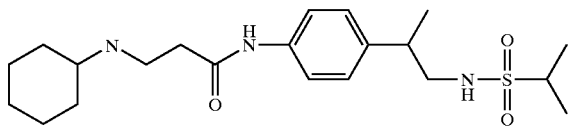

The product of Preparation 4 (0.256 g, 1.0 mmol), N-cyclohexyl-β-alanine (0.171 g, 1.0 mmol), 4-dimethylaminopyridine (0.015 g, 0.12 mmol), 1-[3-dimethylaminopropyl]-3-ethyl carbodiimide hydrochloride (0.384 g, 2.0 mmol), and triethylamine (0.025 g, 0.25 mmol) were placed in methylene chloride (25 mL) and reacted as described in Example 3 to yield an oil (1.67 g). Purification was achieved by chromatotron silica gel chromatography using a 2000 micron rotor and eluting with an isocratic solvent of methylene chloride/methanol 9:1 to yield the title compound (0.031 g) as a clear oil. NMR was consistent with the proposed structure. Ion spray mass spectrum: M+1=410.

EXAMPLE 10

N-2-[4-(2-Ethoxy)acetamido)phenyl]propyl 2-Propanesulfonamide

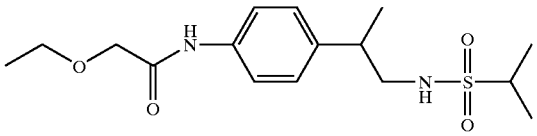

The product of Preparation 4 (0.300 g, 1.17 mmol, 2-ethoxyacetic acid (0.122 g), 1.17 mmol), 4-dimethylaminopyridine (0.011 g, 0.09 mmol), 1-[3-dimethylaminopropyl]-3-ethyl carbodiimide hydrochloride (0.269 g, 1.4 mmol), and triethylamine (0.300 g, 3.0 mmol) were placed in methylene chloride (25 mL) and stirred overnight under nitrogen at ambient temperature. In the morning, the reaction mixture was diluted with an additional 25 mL methylene chloride and the organic solution was washed once with water, dried over $K_2CO_3$, and concentrated under reduced pressure to yield a semi-solid (1.41 g). Purification was achieved by chromatotron silica gel chromatography using a 4000 micron rotor and eluting with an isocratic solvent of methylene chloride/ethyl acetate 1:1 to yield the title compound (0.060 g) as a white solid m.p. 113°–116° C. The NMR spectrum was consistent with the proposed structure. Ion spray mass spectrum: M+1 343.1

Analysis calculated for $C_{16}H_{26}N_2O_4S$: %C, 56.12; %H, 7.65; %N, 8.18. Found: %C, 56.21; %H, 7.61; %N, 8.16.

EXAMPLE 11

N-2-[4-(2-Methoxyacetamido)phenyl]propyl 2-Propanesulfonamide

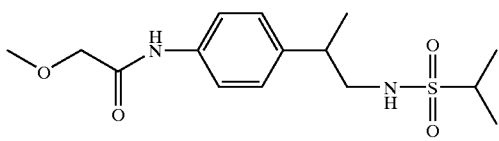

The product of Preparation 4 (0.300 g, 1.17 mmol), 2-methoxyacetic acid (0.106 g, 1.17 mmol), 4-dimethylaminopyridine (0.011 g, 0.09 mmol), 1-[3-dimethylaminopropyl]-3-ethyl carbodiimide hydrochloride (0.269 g, 1.4 mmol), and triethylamine (0.300 g, 3.0 mmol) were placed in methylene chloride (10 mL) and stirred overnight under nitrogen at ambient temperature. In the morning, the reaction mixture was diluted with an additional 25 mL methylene chloride and the organic solution was washed once with water, dried over $K_2CO_3$, and concentrated under reduced pressure to yield a semi-solid (1.71 g). Purification was achieved by chromatotron silica gel chromatography using a 4000 micron rotor and eluting with an isocratic solvent of methylene chloride/ethyl acetate 9:1 to yield the title compound (72 mg) as a brown oil. The NMR spectrum was consistent with the proposed structure. Ion spray mass spectrum: M+1=329.2 Analysis calculated for $C_{15}H_{24}N_2O_4S$-1$H_2O$: %C, 52.03; %H, 7.57; %N, 8.08. Found: %C, 52.35; %H, 7.72; %N, 7.76.

EXAMPLE 12

N-2-[4-(2-Butoxyacetamido)phenyl]propyl 2-Propanesulfonamide

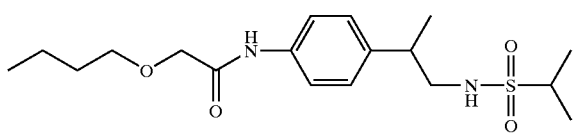

The product of Preparation 4 (0.300 g, 1.17 mmol), 2-butoxyacetic acid (0.155 g, 1.17 mmol), 4-dimethylaminopyridine (0.011 g, 0.09 mmol), 1-[3-dimethylamino-propyl]-3-ethyl carbodiimide hydrochloride (0.269 mg, 1.4 mmol), and triethylamine (0.300 mg, 3.0 mmol) were placed in methylene chloride (10 mL) and stirred overnight under nitrogen at ambient temperature. In the morning, the reaction mixture was diluted with an additional 25 mL methylene chloride and the organic solution was washed once with water, dried over $K_2CO_3$, and concentrated under reduced pressure to yield a semi-solid (1.06 g). Purification was achieved by chromatotron silica gel chromatography using a 4000 micron rotor and eluting with an isocratic solvent of methylene chloride/ethyl acetate 3:2 to yield the title compound (0.121 g) as a clear oil. The NMR spectrum was consistent with the proposed structure. Ion spray mass spectrum: M+1=371.2 Analysis calculated for $C_{18}H_{30}N_2O_4S$: %C, 52.03; %H, 7.57; %N, 8.08. Found: %C, 52.35; %H, 7.72; %N, 7.76.

EXAMPLE 13

N-2-[4-(1-(4-Methyl)piperazinyl)acetamido)phenyl] propyl 2-Propanesulfonamide

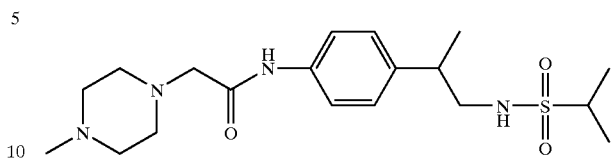

The product of Preparation 5 (0.150 g, 0.59 mmol) and N-methylpiperazine (0.065 g, 1.1 eq.) were placed into toluene (20 mL) and stirred at reflux under nitrogen for 2 hours. The reaction mixture was then cooled to ambient temperature and diluted with 50 mL of 1N sodium hydroxide and 50 mL of ethyl acetate. The organic layer was separated, washed once with water, dried over $K_2CO_3$, and concentrated under reduced pressure to yield an oil (117 mg). Purification was achieved by chromatotron silica gel chromatography using a 1000 micron rotor and eluting with an isocratic solvent of methylene chloride/methanol 9:1 to yield the title compound (0.074 g) as a white solid. m.p. 134°–136° C. The NMR spectrum was consistent with the proposed structure. Ion spray mass spectrum: M+1=379.2.

EXAMPLE 14

N-2-[4-(1-Piperidinylacetamido)-phenyl]propyl 2-Propanesulfonamide

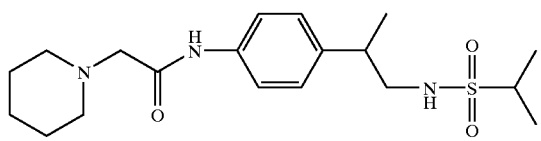

The product of Preparation 5 (0.150 g, 0.59 mmol) and piperidine (0.55 g, 1.1 eq.) were placed into toluene (20 mL) and reacted as described in Example 13 to yield a clear oil (0.175 g). Purification was achieved by chromatotron silica gel chromatography using a 1000 micron rotor and eluting with an isocratic solvent of ethyl acetate to yield the title compound (0.120 g) as a white solid. m.p. 139°–141° C. The NMR spectrum was consistent with the proposed structure. Ion spray mass spectrum: M+1=382.4 Analysis calculated for $C_{19}H_{31}N_3O_3S$: %C, 59.81; %H, 8.19; %N, 11.01. Found: %C, 59.51; %H, 8.29; %N, 11.06.

EXAMPLE 15

N-2-[4-(1-(4-N,N-Dimethylamino)piperidinyl) acetamido-(phenyl]propyl 2-Propanesulfonamide

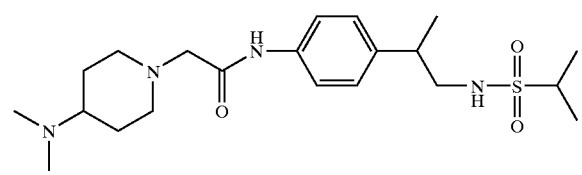

The product of Preparation 5 (0.150 g, 0.59 mmol) and 4-(N,N-dimethylamino)piperidine (0.083 g, 1.1 eq.) were placed into toluene (20 mL) and reacted as described in Example 13 to yield an oil (0.173 g). Purification was achieved by chromatotron silica gel chromatography using a 1000 micron rotor and eluting with a gradient solvent of methanol to methanol/1% ammonium hydroxide to yield the title compound (0.104 g) as a viscous oil. The NMR spectrum was consistent with the proposed structure. Ion spray mass spectrum: M+1=425.3 Analysis calculated for $C_{21}H_{36}N_4O_3S$-0.5$H_2O$: %C, 58.16; %H, 8.60; %N, 12.92. Found: %C, 57.98; %H, 8.61; %N, 12.76.

EXAMPLE 16

N-2-[4-(Propylaminoacetamido)phenyl]propyl 2-Propanesulfonamide

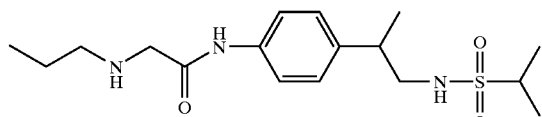

The product of Preparation 5 (0.150 g, 0.59 mmol) and propylamine (50 mg, 1.1 eq.) were placed in toluene (20 mL) and reacted as described in Example 13 to yield an oil (0.179 g). Purification was achieved by chromatotron silica gel chromatography using a 2000 rotor and eluting with an isocratic solvent of methylene chloride/methanol 9:1 to yield the title compound 0.089 g as a clear oil. The NMR spectrum was consistent with the proposed structure. Ion spray mass spectrum: M+1=356.4 Analysis calculated for $C_{17}H_{29}N_3O_3S$-1/2 $H_2O$: %C, 56.01; %H, 8.29; %N, 11.53. Found: %C, 55.91; %H, 7.99; %N, 11.60.

EXAMPLE 17

N-2-(4-(4-(2-(1-Pyrrolidino)ethoxy)phenyl)phenyl) propyl 2-Propanesulfonamide Hydrochloride

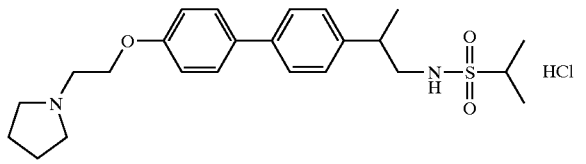

To a stirred solution of 3.05 g (11.3 mmol) of 1-[2-(4-bromophenoxy)ethylpyrrolidine in 50 mL of anhydrous THF under $N_2$ was added 5.0 mL (12.5 mmol) of n-BuLi at −70° C. The mixture was stirred for 30 minutes and 1.5 g (14.2 mmol) of $B(OCH_3)_3$ was added dropwise. Stirring was continued for 1.5 h. at −2 to 5° C. The reaction mixture was then quenched with a saturated solution of ammonium chloride. The THF layer was dried($MgSO_4$), filtered and evaporated in vacuo. The residual glass was dissolved in 50 mL of ethylene glycol dimethyl ether (DME) followed by addition of 3.68 g (12.0 mmol) of N-2-(4-bromophenyl) propyl-2-propanesulfonamide, 0.390 g (0.34 mmol) of palladium tetrakis, 11.3 mL (20.6 mmol) of 2M $Na_2CO_3$ and 2.0 mL (26.8 mmol) of n-propyl alcohol respectively. The resulting mixture was heated and stirred under $N_2$ at reflux for 6 h. The reaction was cooled to ambient temperature, diluted with 100 mL of EtOAc and filtered through celite. Evaporation of the filtrate in vacuo followed by chromatography eluting with 10% $CH_3OH$-90%$CH_2Cl_2$ gave the desired compound (1.79 g) as a light brown oil. Addition of methanolic HCl and recrystallization from $CH_3OH$-EtOAc gave the title compound, mp 172–173° C. Analysis calculated for $C_{24}H_{34}N_2O_3S$.HCl-0.33$H_2O$: C, 60.93; H, 7.59; N, 5.92. Found: C, 60.85; H, 7.34; N, 6.02.

EXAMPLE 18

N-2-(4-(4-(2-(N,N-Dimethylamino)ethoxy)phenyl) phenyl)propyl 2-Propanesulfonamide Hydrochloride

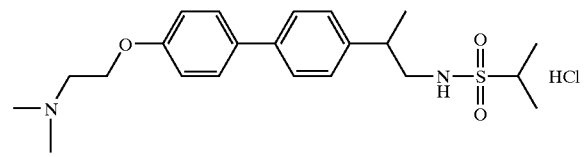

To a stirred solution of 4-(N,N-dimethylaminoethoxy)-phenyl bromide (1.0 g, 4.10 mmol) in 20 mL of THF under $N_2$ was added 2.1 mL (5.33 mmol) of a 2.5 M solution of n-BuLi at −78° C. The mixture was stirred for 30 minutes and 0.56 mL (4.92 mmol) of trimethyl borate was added dropwise. Stirring was continued for 1.5 hours at −2 to 5° C. then the reaction mixture was concentrated in vacuo. The resulting residual solid was dissolved in 20 mL of of ethylene glycol dimethyl ether (DME) followed by addition of 1.0 g (3.12 mmol) the product of Preparation 8 0.14 g (0.12 mmol) of tetrakis (triphenylphosphine)palladium(0), 3.12 mL (6.24 mmol)of 2 M $Na_2CO_3$ and 0.47 mL (6.24 mmol) of n-propyl alcohol, respectively. The resulting mixture was heated at reflux while stirring under $N_2$ for 6 hours. The reaction mixture was allowed to cool to ambient temperature, diluted with 30 mL of ethyl acetate and filtered through Celite. Evaporation of the filtrate in vacuo followed by chromatography, eluting with 95:5 methylene chloride/methanol gave 0.22 g of the desired compound as a yellow oil. The residue was dissolved in ether and a saturated solution of HCl in methanol was added dropwise until precipitation of a solid was observed. The ether was decanted off and the resulting solid was triturated several times with ethyl acetate to afford the title compound as a white solid. $^1$H NMR (400 MHz, $CDCl_3$): δ 1.29 (9H, m), 2.93 (6H, s), 2.94–3.16 (2H, m), 3.19–3.39 (2H, m), 2.44 (2H, t), 4.00 (1H, t), 4.71 (2H, t), 6.91–7.52 (8H, m), 12.93 (1H, s).

EXAMPLE 19

N-2-(4-(4-(2-Hydroxy)ethoxy)phenyl)phenyl)propyl 2-Propanesulfonamide

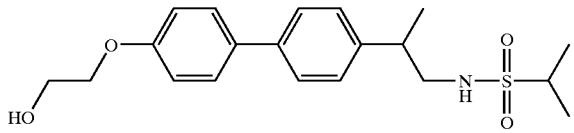

2-(4-Bromophenoxy)ethanol (0.50 g, 2.30 mmol) was dissolved in 15 mL of THF and stirred at 0° C. under $N_2$. 0.10 g (2.53 mmol) of a 60% oil dispersion of sodium hydride was added in small portions and the mixture was stirred for 30 min. then cooled to −78° C. followed by the addition of 1.3 mL (2.53 mmol) of a 2.5 M solution of n-BuLi. The mixture was stirred for 30 minutes and 0.58 mL (2.53 mmol) of triisopropyl borate was added dropwise. Stirring was continued for 1.5 hours at −2 to 5° C. then the reaction mixture was quenched with a 1.0 M solution of HCl. The layers were separated and the organic phase was dried (MgSO$_4$) and concentrated. The resulting oil was dissolved in 10 mL of of ethylene glycol dimethyl ether (DME) followed by addition of 0.51 g (1.60 mmol) of the product of Preparation 8, 0.074 g (0.064 mmol) of tetrakis (triphenylphosphine)palladium(0), 1.60 mL (3.20 mmol) of 2 M Na$_2$CO$_3$ and 0.24 mL (3.20 mmol) of n-propyl alcohol, respectively. The resulting mixture was heated at reflux while stirring under N$_2$ for 8 hours. The reaction mixture was allowed to cool to ambient temperature. 5 mL of H$_2$O were added and the layers were separated. The aqueous layer was extracted with ether and the organics were combined, washed with saturated NaCl and H$_2$O, dried (MgSO$_4$) and concentrated to a brown oil. Chromatography, eluting with 99:1 methylene chloride/methanol gave 0.07 g (20 %) of a light yellow solid. Recrystallization from hexanes/methylene chloride yielded the desired compound. $^1$H NMR (400 MHz, CDCl$_3$): δ 1.23 (9H, m), 2.16 (1H, s), 2.96–3.12 (2H, m), 3.21–3.39 (2H, m), 3.97 (2H, t), 4.11 (2H, t), 6.96–7.48 (8H, m); LRMS (ES$^-$) 376.4 M–H; Anal. Calculated for C$_{20}$H$_{27}$NSO$_4$: %C, 63.63; %H, 7.21; %N, 3.71. Found %C, 63.70; %H, 7.15; %N, 3.96.

EXAMPLE 20

N-2-[4-(2-(N,N-Dimethylamino)ethoxy)phenyl] propyl 2-Propanesulfonamide

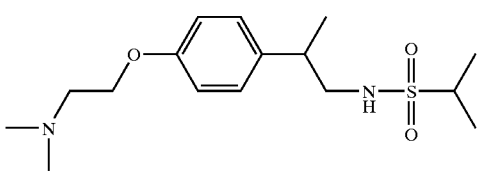

The product of Preparation 12 (0.250 g, 0.7 mmol) was dissolved in dimethylformamide and sodium hydride (0.031 g, 0.77 mmol) was added. After 15 minutes, 2-N'N-dimethylaminoethyl chloride hydrochloride (0.126 g, 0.77 mmol), potassium carbonate (0.128 g, 0.93 mmol) and potassium iodide (0.035 g, 0.21 mmol) were added to the reaction and the mixture was stirred at 65° C. for 2 hours. The reaction mixture was partitioned between dichloromethane and water. The organic was washed with brine, dried over sodium sulfate and concentrated in vacuo. Chromatography (SiO$_2$, 5% methanol/dichloromethane) gave 0.101 g (34%) of the pure product which was dissolved in 2 mL of the dichloromethane: TFA (1:1). The mixture was stirred at ambient temperature for 45 minutes. The reaction mixture was partitioned between dichloromethane and water. The organic layer was dried over sodium sulfate and concentrated in vacuo to give 0.077 g (91%) of the title compound.

Electrospray Mass Spectrum: M=329.3; Analysis calculated for C$_{16}$H$_{28}$N$_2$O$_3$S.0.25H$_2$O: %C, 57.71; %H, 8.63; %N, 8.41. Found: %C, 57.84; %H, 8.37; %N, 8.44.

EXAMPLE 21

N-2-[4-(3-(N,N-Dimethylamino)propoxy)phenyl] propyl 2-Propanesulfonamide

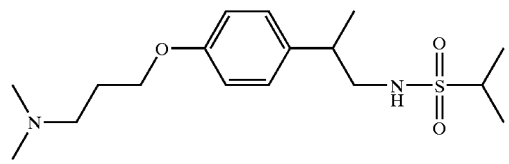

The title compound was prepared from the product of Preparation 12 and 3-N,N-dimethylaminopropyl chloride hydrochloride as described in Example 20. Electrospray Mass Spectrum: M=343.1 Analysis calculated for C$_{17}$H$_{30}$N$_2$O$_3$S-0.5H$_2$O: %C, 58.84; %H, 8.86; %N, 8.07. Found: %C, 59.00; %H, 8.66; %N, 7.50.

EXAMPLE 22

N-2-([4-(2-(1-Piperidinyl)ethoxy)phenyl]propyl 2-Propanesulfonamide

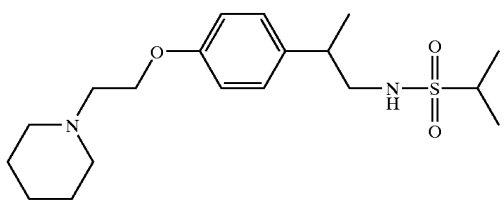

The title compound was prepared from the product of Preparation 12 and 2-(1-piperidinyl)ethyl chloride as described in Example 20. Electrospray Mass Spectrum: M=369.1; Analysis calculated for C$_{19}$H$_{32}$N$_2$O$_3$S: %C, 61.92; %H, 8.75; %N, 7.60. Found: %C, 61.98; %H, 8.27; %N, 6.99.

EXAMPLE 23

N-2-[4-(3-(1-Piperidinyl)propoxy)phenyl]propyl 2-Propanesulfonamide

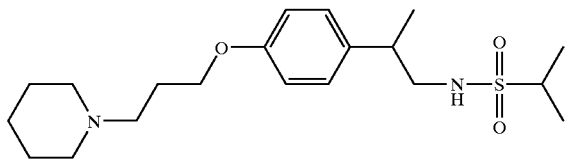

The title compound was prepared from the product of Preparation 12 and 3-(1-piperidinyl)propyl chloride as described in Example 20. Electrospray Mass Spectrum: M=383.4. Analysis calculated for C$_{20}$H$_{34}$N$_2$O$_3$S: %C, 61.92; %H, 8.75; %N, 7.60. Found: %C, 61.98; %H, 8.27; %N, 6.99.

EXAMPLE 24

N-2-[4-(4-Chlorophenoxymethyl)oxy)phenyl]propyl 2-Propanesulfonamide

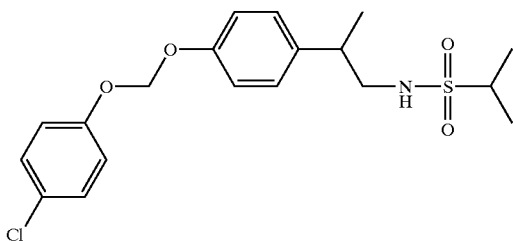

The product of Preparation 12 (0.250 g, 0.7 mmol) was dissolved in dimethylformamide and sodium hydride (0.034 g, 0.84 mmol) was added. After 30 minutes α-4-dichloroanisole (0.136 g, 0.77 mmol) and potassium iodide (0.025 g, 0.14 mmol) were added to the reaction and the mixture was stirred at 65° C. for 2 hours. The reaction mixture was partitioned between ethyl acetate and water. The organic was washed with brine, dried over sodium sulfate and concentrated in vacuo. The crude product was dissolved in 2 mL of the dichloromethane: TFA (1:1). The mixture was stirred at ambient temperature for 45 minutes. The reaction mixture was partitioned between dichloromethane and water. The organic was dried over sodium sulfate and concentrated in vacuo to give 0.172 g (62%) of the title compound. Electrospray Mass Spectrum: M=396. Analysis calculated for $C_{19}H_{24}ClNO_4S$: %C, 57.35; %H, 6.08; %N, 3.52. Found: %C, 57.90; %H, 6.10; %N, 3.56.

EXAMPLE 25

N-2-[4-(2-Phenoxyethyl)oxy)phenyl]propyl 2-Propanesulfonamide

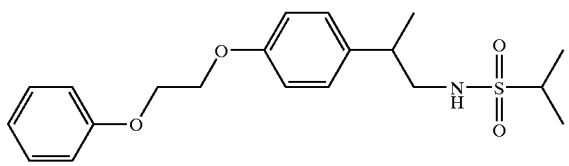

The title compound was prepared from the product of Preparation 12 and phenoxyethyl chloride as described in Example 24. Electrospray Mass Spectrum: M=377.5; Analysis calculated for $C_{20}H_{27}NO_4S$: %C, 63.63; %H, 7.21; %N, 3.71. Found: %C, 63.70; %H, 7.46; %N, 3.85.

EXAMPLE 26

N-2-[4-(2-(4-Acetamido)phenyloxyethoxy)phenyl] propyl 2-Propanesulfonamide

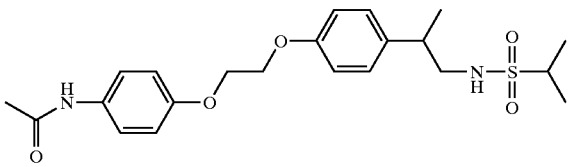

4-Acetamidophenol (0.091 g, 0.6 mmol) was dissolved in 3 mL dimethylformamide and sodium hydride (0.024 g, 0.75 mmol) was added. After 3.0 minutes the product of Preparation 13 (0.250 g, 0.6 mmol) and potassium iodide (0.025 g, 0.15 mmol) were added to the reaction and the mixture was stirred at 65° C. for 4 hours. The reaction mixture was partitioned between ethyl acetate and water. The organic layer was washed with brine, dried over sodium sulfate and concentrated in vacuo. Chromatography ($SiO_2$, 5% methanol/dichloromethane) gave 0.164 g (51%) of the pure product. The resulted product was dissolved in 2 mL of the dichloromethane: TFA (1:1). The mixture was stirred at. ambient temperature for 1 minute. The reaction mixture was then partitioned between dichloromethane and water. The organic was washed with brine, dried over sodium sulfate and concentrated in vacuo to give 0.090 g (74%) of the title compound. Electrospray Mass Spectrum: M=435.4; Analysis calculated for $C_{22}H_{30}N_2O_5S$: %C, 60.81; %H, 6.96; %N, 6.45. Found: %C, 60.84; %H, 7.16; %N, 6.72.

EXAMPLE 27

N-2-[4-(2-(3-Acetamido)phenyloxyethoxy)phenyl] propyl 2-Propanesulfonamide

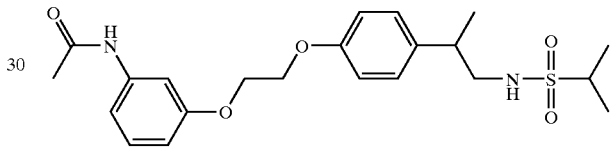

The title compound was prepared from the product of Preparation 13 and 3-acetamidophenol as described in Example 26. Electrospray Mass Spectrum: 435.4 Analysis calculated for $C_{22}H_{30}N_2O_5S$: %C, 60.81; %H, 6.96; %N, 6.45. Found: %C, 60.29; %H, 6.88; %N, 6.36.

EXAMPLE 28

N-2-[4-((2-Acetamido)phenyloxyethoxy)phenyl) propyl 2-Propanesulfonamide

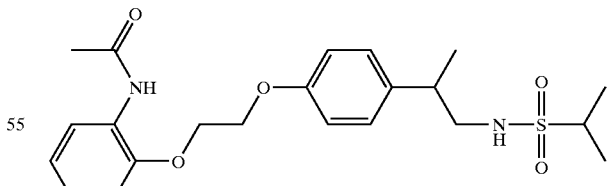

The title compound was prepared from the product of Preparation 13 and 2-acetamidophenol as described in Example 26. Electrospray Mass Spectrum: 435.3. Analysis calculated for $C_{22}H_{30}N_2O_5S$-$0.1CF_3COOH$: %C, 59.79; %H, 6.80; %N, 6.28. Found: %C, 59.46; %H, 6.49; %N, 6.24.

EXAMPLE 29

N-2-(4-(2-Phenoxyethoxy)-phenyl)-propyl-2-propanesulfonamide

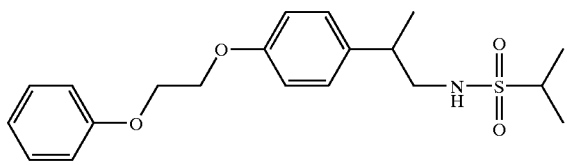

To a stirred mixture of N-tertbutoxyacetyl-2-(4-hydroxyphenyl)propyl-2-propanesulfonamide (0.250 g, 70 mmol) in dry dimethylformamide (4 mL) was added sodium hydride (0.062 g, 0.87 mmol) under nitrogen. The resulting mixture was stirred 30 minutes at ambient temperature or until hydrogen gas evolution had ceased. Next, β-chlorophenetole (0.120 g, 0.77 mmol) and sodium iodide (0.042 g, 0.25 mmol) are added and the resulting mixture was heated to 65° C. for 12 h. The resulting mixture was cooled and partitioned between ethyl acetate and water. The organic layer was washed with water (2×20 mL) and brine (1×20 mL), dried over magnesium sulfate, and filtered. Evaporation of the filtrate in vacuo followed by chromatography on silica gel eluting with ethyl acetate-hexane gave 0.250 g (75%) of the protected sulfonamide. To a stirred mixture of dichloromethane: trifluoroacetic acid (2 mL, 1:1) was added the protected sulfonamde (0.220 g, 0.42 mmol) under nitrogen. The resulting mixture was stirred at ambient temperature for 4 h. The mixture was partitioned between dichloromethane and 10% aqueous potassium carbonate. The organic layer was washed with brine (1×20 mL), dried over magnesium sulfate, and filtered. Evaporation of the filtrate in vacuo gives 0.166 g (96%) of the pure title compound.

Mass Spectrum: $MS^{+1}$=378.5; Analysis for $C_{20}H_{27}NO_4S$: Theory: C, 63.63; H, 7.21; N, 3.71. Found: C, 63.70; H, 7.46; N, 3.85.

EXAMPLE 30

Specific Preparation of N-2-(4-(2-(2-Acetamidophenoxy)-ethoxy)-phenyl)-propyl-2-propanesulfonamide

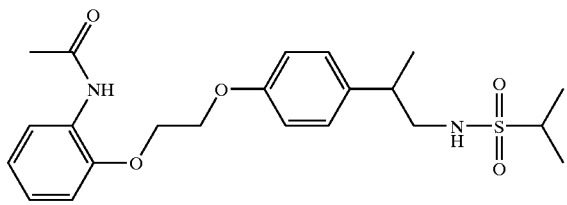

To a stirred mixture of 2-hydroxyacetanilide (0.091 g, 0.60 mmol) in dry dimethylformamide (3 mL) was added sodium hydride (0.030 g, 0.75 mmol) under nitrogen. The resulting mixture was stirred 30 minutes at ambient temperature or until hydrogen gas evolution had ceased. Next, N-tertbutoxyacetyl-2-[(4-(2-chloroethoxy)-phenyl)-propyl]-2-propanesulfonamide (0.250 g, 0.60 mmol) and sodium iodide (0.025 g, 0.15 mmol) are added and the resulting mixture is heated to 65° C. for 12 h. The resulting mixture was cooled and partitioned between ethyl acetate and water. The organic layer was washed with water (2×20 mL) and brine (1×20 mL), dried over magnesium sulfate, and filtered. Evaporation of the filtrate in vacuo followed by chromatography on silica gel eluting with ethyl acetate-hexane gave 0.100 g (31%) of the protected sulfonamide. To a stirred mixture of dichloromethane:trifluoroacetic acid (2 mL, 1:1) was added the protected sulfonamde (0.100 g, 0.19 mmol) under nitrogen. The resulting mixture was stirred at ambient temperature for 4 h. The mixture was partitioned between dichloromethane and 10% aqueous potassium carbonate. The organic layer was washed with brine (1×20 mL), dried over magnesium sulfate, and filtered. Evaporation of the filtrate in vacuo followed by chromatography on silica gel eluting with ethyl acetate-hexane gave 0.080 g (98%) of the pure title compound.

Mass Spectrum: $MS^{+1}$=435.3.

EXAMPLE 31

N-2-(4-(2-(2-Fluorophenoxy)-ethoxy)-phenyl)-propyl-2-propanesulfonamide

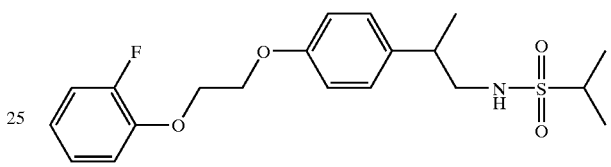

The title compound was prepared from the product of preparation 14 and 2-fluorophenol in a manner analogous to Example 30.

Mass Spectrum: $MS^{+1}$=396.1; Analysis for $C_{20}H_{26}FNO_4S$: Theory: C, 60.74; H, 6.63; N, 3.54. Found: C, 60.63; H, 6.71; N, 3.44.

EXAMPLE 32

N-2-(4-(2-(3-Fluorophenoxy)-ethoxy)-phenyl)-propyl-2-propanesulfonamide

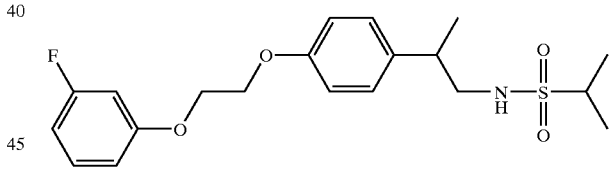

The title compound was prepared from the product of Preparation 14 and 3-fluorophenol in a manner analogous to Example 30.

Mass Spectrum: $MS^{+1}$=396.0.

EXAMPLE 33

N-2-(4-(2-(4-Fluorophenoxy)-ethoxy)-phenyl)-propyl-2-propanesulfonamide

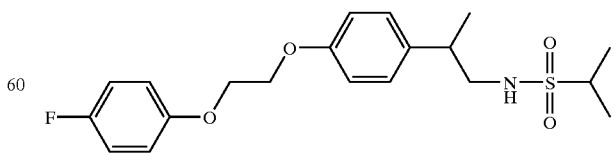

The title compound was prepared from the product of Preparation 14 and 4-fluorophenol in a manner analogous to Example 30.

Mass Spectrum: $MS^{+1}=396.1$; Analysis for $C_{20}H_{26}FNO_4S$: Theory: C, 60.74; H, 6.63; N,. 3.54. Found: C, 60.85; H, 6.60; N, 3.79.

EXAMPLE 34

N-2-(4-(2-(3-Trifluoromethylphenoxy)-ethoxy)-phenyl)-propyl-2-propanesulfonamide

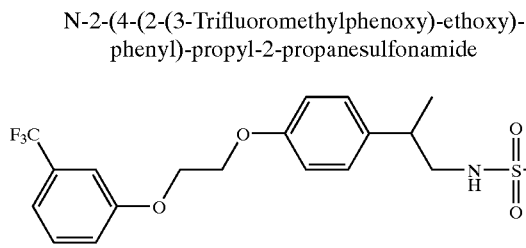

The title compound was prepared from the product of Preparation 14 and 3-hydroxybenzotrifluoride in a manner analogous to Example 30.

Mass Spectrum: $MS^{-1}=444.3$; Analysis for $C_{21}H_{26}F_3NO_4S+0.8H_2O$: Theory: C, 54.84; H, 6.05; N, 3.04. Found: C, 54.44; H, 6.28; N, 3.02.

EXAMPLE 35

N-2-(4-(2-(4-Trifluoromethylphenoxy)-ethoxy)-phenyl)-propyl-2-propanesulfonamide

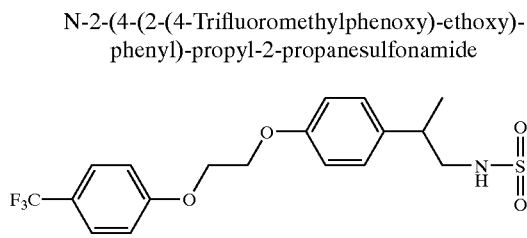

The title compound was prepared from the product of Preparation 14 and 4-hydroxybenzotrifluoride in a manner analogous to Example 30.

Mass Spectrum: $MS^{-1}=444.2$; Analysis for $C_{21}H_{26}F_3NO_4S$: Theory: C, 56.62; H, 5.88; N, 3.14. Found: C, 56.85; H, 5.94; N, 3.32.

EXAMPLE 36

N-2-(4-(2-(2,3-Difluorophenoxy)-ethoxy)-phenyl)-propyl-2-propanesulfonamide

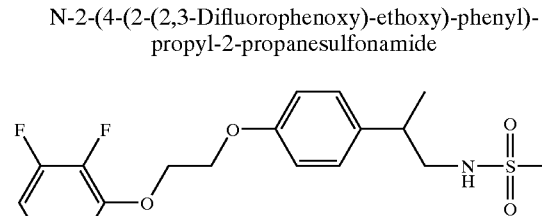

The title compound was prepared from the product of Preparation 14 and 2,3-difluorophenol in a manner analogous to Example 30.

Mass Spectrum: $MS^{-1}=414.2$; Analysis for $C_{20}H_{25}F_2NO_4S$: Theory: C, 58.10; H, 6.09; N, 3.39. Found: C, 58.17; H, 6.39; N, 3.45.

EXAMPLE 37

N-2-(4-(2-(2-Cyanophenoxy)-ethoxy)-phenyl)-propyl-2-propanesulfonamide

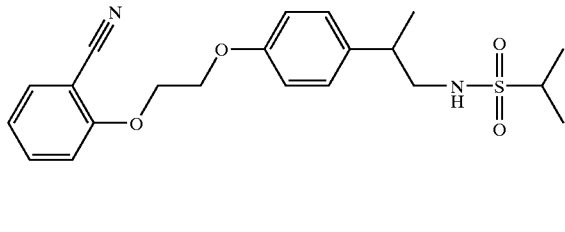

The title compound was prepared from the product of Preparation 14 and 2-cyanophenol in a manner analogous to Example 30.

Mass Spectrum: $MS^{+1}=403.4$; Analysis for $C_{21}H_{26}N_2O_4S+0.25H_2O$ : Theory: C, 61.97; H, 6.56; N, 6.88. Found: C, 61.66; H, 6.54; N, 6.61.

EXAMPLE 38

N-2-(4-(2-(3-Cyanophenoxy)-ethoxy)-phenyl)-propyl-2-propanesulfonamide

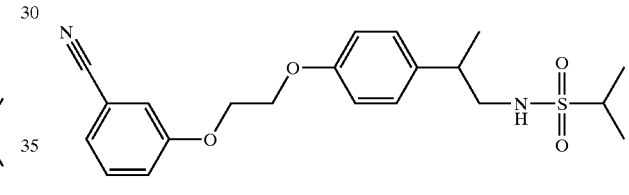

The title compound was prepared from the product of Preparation 14 and 3-cyanophenol in a manner analogous to Example 30.

Mass Spectrum: $MS^{+1}=403.4$; Analysis for $C_{21}H_{26}N_2O_4S$: Theory: C, 62.66; H, 6.51; N, 6.96. Found: C, 62.56; H, 6.39; N, 6.76.

EXAMPLE 39

N-2-(4-(2-(4-Cyanophenoxy)-ethoxy)-phenyl)-propyl-2-propanesulfonamide

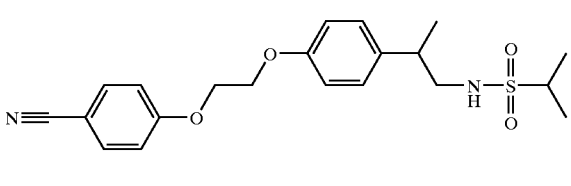

The title compound was prepared from the product of Preparation 14 and 4-cyanophenol in a manner analogous to Example 30.

Mass Spectrum: $MS^{+1}=403.4$.

EXAMPLE 40

N-2-[(4-(2-(2-Chlorophenoxy)-ethoxy)-phenyl)-propyl]-2-propanesulfonamide

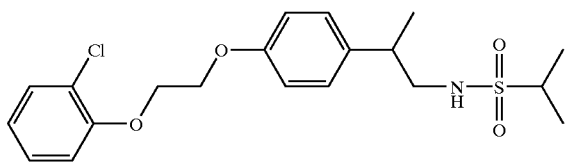

The title compound was prepared from the product of Preparation 14 and 2-cyanophenol in a manner analogous to Example 30.

Mass Spectrum: $MS^{+1}=412.1$.

EXAMPLE 41

N-2-(4-(2-(2-Methoxyphenoxy)-ethoxy)-phenyl)-propyl-2-propanesulfonamide

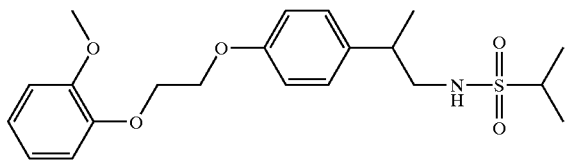

The title compound was prepared from the product of Preparation 14 and guaiacol in a manner analogous to Example 30.

Mass Spectrum: $MS^{+1}=408.4$.

EXAMPLE 42

N-2-[(4-(2-(2-Fluorothiophenoxy)-ethoxy)-phenyl)-propyl]-2-propanesulfonamide

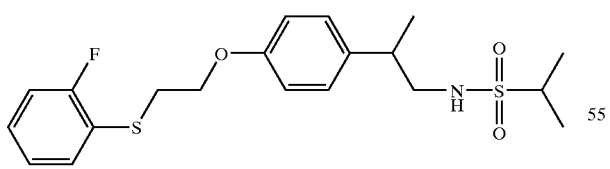

The title compound was prepared from the product of Preparation 14 and 2-fluorothiophenol in a manner analogous to Example 30.

Mass Spectrum: $MS^{-1}=410.3$; Analysis for $C_{20}H_{26}FNOS_2+0.3H_2O$: Theory: C, 57.61; H, 6.43; N, 3.36. Found: C, 57.23; H, 6.75; N, 3.33.

EXAMPLE 43

N-2-[(4-(2-(Thiophenoxy)-ethoxy)-phenyl)-propyl]-2-propanesulfonamide

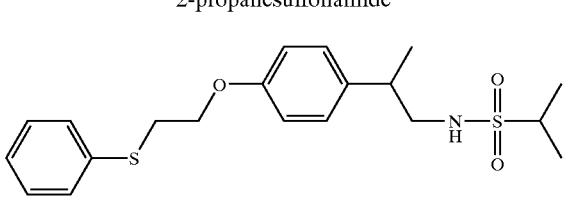

The title compound was prepared from the product of Preparation 14 and benzenephenol in a manner analogous to Example 30.

Mass Spectrum: $MS^{-1}=392.2$.

EXAMPLE 44

N-2-(4-(2-(3-Pyridyloxy)-ethoxy)-phenyl)-propyl-2-propanesulfonamide

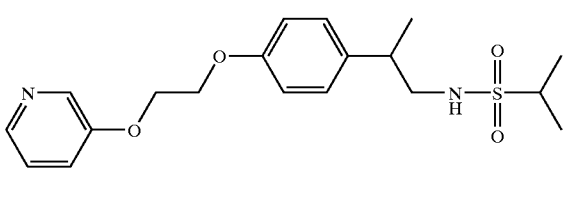

The title compound was prepared from the product of Preparation 14 and 3-hydroxypyridine in a manner analogous to Example 30.

Mass Spectrum: $MS^{+1}=379.5$; Analysis for $C_{19}H_{26}N_2O_4S$: Theory: C, 60.29; H, 6.92; N, 7.40. Found: C, 60.04; H, 7.14; N, 7.15.

EXAMPLE 45

N-2-(4-(2-(N'-2-Pyridinone)-ethoxy)-phenyl)-propyl-2-propanesulfonamide

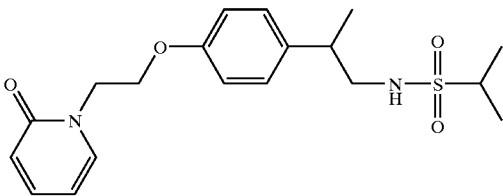

The title compound was prepared from the product of Preparation 14 and 2-hydroxypyridine in a manner analogous to Example 30.

Mass Spectrum: $MS^{+1}=379.4$; Analysis for $C_{19}H_{26}N_2O_4S+0.15H_2O$: Theory: C, 59.86; H, 6.95; N, 7.35. Found: C, 59.50; H, 6.97; N, 7.07.

EXAMPLE 46

N-2-(4-(2-(2-Pyrimidyloxy)-ethoxy)-phenyl)-propyl-2-propanesulfonamide

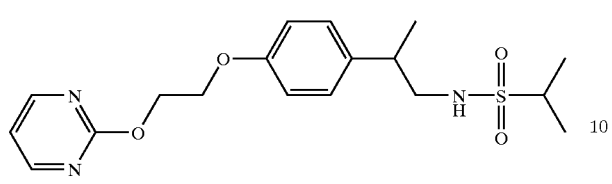

The title compound was prepared from the product of Preparation 14 and 2-hydroxypyridine in a manner analogous to Example 30.

Mass Spectrum: $MS^{-1}=380.4$; Analysis for $C_{18}H_{25}N_3O_4S$: Theory: C, 56.97; H, 6.64; N, 11.07. Found: C, 57.16; H, 6.72; N, 10.93.

EXAMPLE 47

N-2-(4-(2-(Methoxy)-ethoxy)-phenyl)-propyl-2-propanesulfonamide

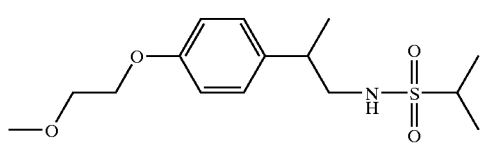

The title compound was prepared from N-tertbutoxyacetyl-2-(4-hydroxyphenyl)propyl-2-propanesulfonamide [the product of Preparation 12] and 2-bromoethylmethylether in a manner analogous to Example 29.

Mass Spectrum: $MS^{+1}=316.1$; Analysis for $C_{15}H_{25}NO_4S+0.15H_2O$: Theory: C, 56.63; H, 8.02; N, 4.40. Found: C, 56.64; H, 7.62; N, 4.56.

EXAMPLE 48

N-2-(4-(2-(Ethoxy)-ethoxy)-phenyl)-propyl-2-propanesulfonamide

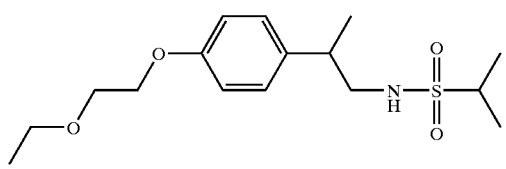

The title compound was prepared from N-tertbutoxyacetyl-2-(4-hydroxyphenyl)propyl-2-propanesulfonamide [the product of Preparation 12] and 2-bromoethylethylether in a manner analogous to Example 29.

Mass Spectrum: $MS^{+1}=330.2$; Analysis for $C_{16}H_{27}NO_4S$: Theory: C, 58.33; H, 8.26; N, 4.25. Found: C, 58.05; H, 8.15; N, 4.28.

EXAMPLE 49

N-2-(4-(2-(2-Methoxyethoxy)-ethoxy)-phenyl)-propyl-2-propanesulfonamide

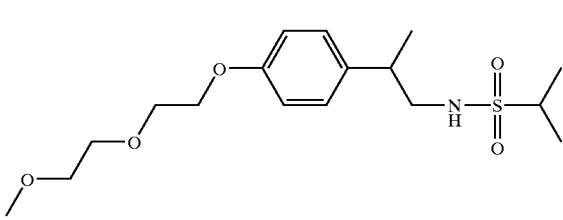

The title compound was prepared from N-tertbutoxyacetyl-2-(4-hydroxyphenyl)propyl-2-propanesulfonamide [the product of Preparation 12] and 1-bromo-2-(2-methoxyethoxy)ethane in a manner analogous to Example 29.

Mass Spectrum: $MS^{+1}=360.2$.

EXAMPLE 50

N-2-(4-(3-(Phenoxy)-propoxy)-phenyl)-propyl-2-propanesulfonamide

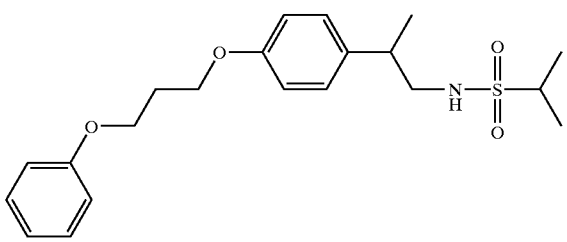

The title compound was prepared from N-tertbutoxyacetyl-2-(4-hydroxyphenyl)propyl-2-propanesulfonamide (the product of Preparation 12] and 3-bromopropylphenylether in a manner analogous to Example 29.

Mass Spectrum: $MS^{-1}=390.3$.

EXAMPLE 51

N-2-(4-(3-(Phenoxy)-butoxy)-phenyl)-propyl-2-propanesulfonamide

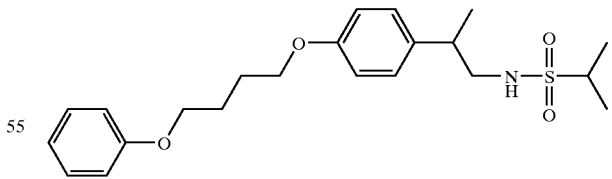

The title compound was prepared from N-tertbutoxyacetyl-2-(4-hydroxyphenyl)propyl-2-propanesulfonamide (the product of Preparation 12] and 4-phenoxybutylbromide in a manner analogous to Example 29.

Mass Spectrum: $MS^{-1}=404.5$; Analysis for $C_{22}H_{31}NO_4S$: Theory: C, 65.16; H, 7.70; N, 3.45. Found: C, 65.45; H, 7.83; N, 3.62.

EXAMPLE 52

N-2-(4-(4-(2-Acetoxyethyl)phenoxy)phenyl)propyl-2-propanesulfonamide

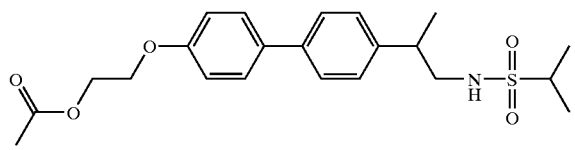

N-2-(4-(4-(2-hydroxy)ethoxy)phenyl)phenyl)propyl 2-propanesulfonamide (0.10 g, 0.27 mmol, prepared in example 19) was combined with 4-dimethylaminopyridine (0.003 g, 0.027 mmol) in dry acetonitrile (3 mL). Acetyl chloride (23 μL, 0.32 mmol) was added and the reaction was stirred at room temperature under $N_2$ for 24 h. The reaction mixture was concentrated to a yellow foam which was dissolved in $CH_2Cl_2$ and washed with 1 M HCl, saturated $NaHCO_3$, dried ($MgSO_4$) and concentrated to a white crystalline solid.

LRMS(ES⁻): 418.3 (M−1); Anal. Calc'd for $C_{22}H_{29}NSO_5$: C 62.98, H 6.97, N 3.34; Found C 63.14, H 6.85, N 3.27.

EXAMPLE 53

N-2-(4-(4-(2-(N-Phenylcarbamoyl)ethyl)phenoxy)propyl-2-propanesulfonamide

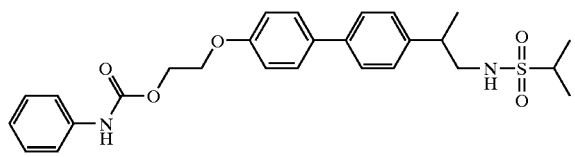

N-2-(4-(4-(2-Hydroxy)ethoxy)phenyl)phenyl)propyl 2-propanesulfonamide (0.05 g, 0.13 mmol, prepared in example 19) and phenylisocyanate (14.0 μL, 0.13 mmol) were combined in dry $CH_2Cl_2$ and heated at 40° C. for 3 h. while stirring under $N_2$ then cooled to room temperature and stirred overnight. The reaction mixture was concentrated to a brown oil which was purified by chromatotron (1 mm plate, Harrison Research Inc., Palo Alto, Calif.) eluting with 1:4 (v/v) ethyl acetate/hexanes to give 0.065 g (100%) of the title compound as a white solid.

¹HNMR (400 MHz, $CDCl_3$): δ 1.29 (9H, m), 2.94–3.14 (2H, m) 3.19–3.40 (2H, m), 4.08 (1H, t), 4.22 (2H, t), 4.57 (2H, t), 6.82–7.56 (13H, m); LRMS(ES⁺): 497.2 (M+1); LRMS(ES⁻): 495.2 (M−1).

EXAMPLE 54

N-2-(4-(4-(2-(N-Ethylcarbamoyl)ethyl)phenoxy)propyl-2-propanesulfonamide

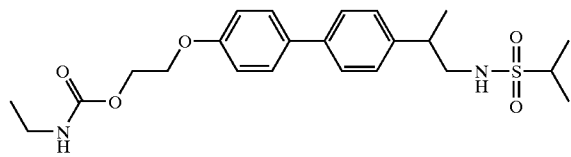

The title compound was prepared from N-2-(4-(4-(2-hydroxy)ethoxy)phenyl)phenyl)propyl 2-propanesulfonamide (prepared in example 19) and ethyl isocyanate as described in Example 53. Purification (30% ethyl acetate/70% hexanes) yielded 0.053 g (92%) of product as a white solid.

¹HNMR (400 MHz, $CDCl_3$): δ 1.22 (9H, m), 2.87–3.09 (2H, m), 3.18 (3H, m), 3.31 (1H, m), 3.80 (1H, t), 4.17 (2H, t), 4.39 (2H, t), 4.63 (1H, br, s), 6.94 (2H, d), 7.20 (2H, d), 7.42 (4H, m). LRMS(ES⁺): 449.1 (M+1); LRMS(ES⁻): 447.2 (M−1).

EXAMPLE 55

N-2-(4-(4-(2-(O-Methanesulfonyl)ethyl)phenoxy)propyl-2-propanesulfonamide

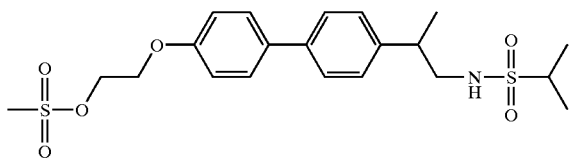

Triethylamine (138.0 μL, 0.99 mmol) was added dropwise to a solution of N-2-(4-(4-(2-hydroxy)ethoxy)phenyl) phenyl)propyl 2-propanesulfonamide (prepared in example 19) in dry $CH_2Cl_2$ (6 mL) at room temperature while stirring under $N_2$. After 15 min., methanesulfonyl chloride (61.0 μL, 0.79 mmol) was added dropwise and the reaction was stirred for 4 h. at room temp. The reaction mixture was concentrated in vacuo and the crude residue was purified by chromatography (30% ethyl acetate/70% hexanes) to give 0.30 g (100%) of the title compound. This compound was sufficiently pure to be used in the next step.

EXAMPLE 56

N-2-(4-(4-(2-Azidoethyl)phenoxy)propyl-2-propanesulfonamide

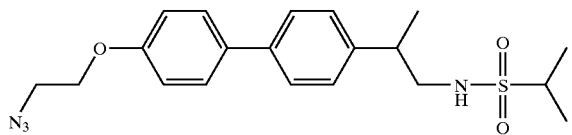

N-2-(4-(4-(2-(O-methanesulfonyl)ethyl)phenoxy)propyl-2-propanesulfonamide (0.30 g, 0.66 mmol, prepared in example 55) was combined with lithium azide (0.16 g, 3.3 mmol) in dry dimethylformamide (6 mL) and heated at reflux while stirring under $N_2$ for 3 h. The reaction mixture was cooled to room temp. and concentrated in vacuo. The crude residue was purified by chromatography (1:1 (v/v) ethyl acetate/hexanes) to give 0.13 g (48%) of the title compound as a white crystalline solid.

LRMS(ES⁻): 401.2 (M−1); Anal. Calc'd for $C_{20}H_{26}N_4SO_3$: C 59.68, H 6.72, N 13.29; Found C 59.56, H 6.72, N 13.11.

EXAMPLE 57

N-2-(4-(4-(2-Aminoethyl)phenoxy)propyl-2-propanesulfonamide Hydrochloride

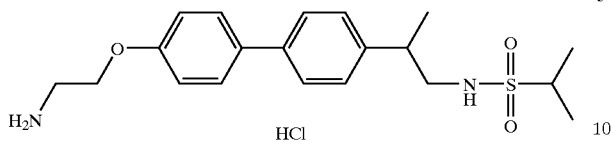

N-2-(4-(4-(2-Azidoethyl)phenoxy)propyl-2-propanesulfonamide (0.10 g, 0.25 mmol, prepared in example 56) was combined with triphenylphosphine (0.079 g, 0.30 mmol) in THF (2 mL) and H$_2$O (0.2 mL) and the reaction was heated at reflux overnight. The reaction mixture was cooled to room temp. and concentrated in vacuo. The crude residue was taken up in ethyl acetate and HCl gas was bubbled through the solution until a white precipitate formed. The solid was collected by vacuum filtration and washed with ethyl acetate.

MS(ES$^+$): 377.4 (M+1); MS(ES$^-$): 375.3 (M−1); Anal. Calc'd for C$_{20}$H$_{28}$N$_2$O$_3$S.HCl (1/4 H$_2$O): C 56.92, H 7.16, N 6.64; Found C 56.78, H 7.06, N 6.54.

EXAMPLE 58

N-2-(4-(4-(2-(4-N-Morpholino)ethyl)phenoxy)phenyl)propyl-2-propanesulfonamide

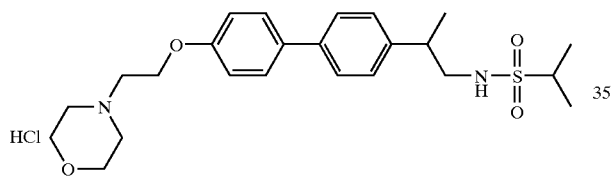

To a stirred solution of 4-(2-(4-morpholine)ethoxy)phenyl bromide (1.0 g, 3.5 mmol) in 25 mL of THF under N$_2$ was added 1.8 mL (4.54 mmol) of a 2.5 M solution of n-BuLi at −78° C. The mixture was stirred for 30 minutes and 0.48 mL (4.19 mmol) of trimethyl borate was added dropwise. Stirring was continued for 1.5 hours at −2 to 5° C. then the reaction mixture was concentrated in vacuo. The resulting residual solid was dissolved in 20 mL of DME followed by addition of 1.0 g (3.12 mmol) of N-2-(4-bromophenyl)propyl-2-propanesulfonamide, 0.14 g (0.12 mmol) of tetrakis(triphenylphosphine)Pd(0), 3.12 mL (6.24 mmol)of 2 M Na$_2$CO$_3$ and 0.47 mL (6.24 mmol) of n-propyl alcohol, respectively. The resulting mixture was heated at reflux while stirring under N$_2$ for 6 hours. The reaction mixture was allowed to cool to ambient temperature, diluted with 30 mL of ethyl acetate and filtered through Celite. Evaporation of the filtrate in vacuo followed by chromatography, eluting with 95:5 methylene chloride/methanol gave 0.22 g (17%) of the desired compound as a yellow oil. The residue was dissolved in ether and a saturated solution of HCl in methanol was added dropwise until precipitation of a solid was observed. The ether was decanted off and the resulting solid was triturated several times with ethyl acetate to afford the title compound as a white solid.

LRMS(ES$^-$): 445.4 (M−1); Anal. Calc'd for C$_{24}$H$_{34}$N$_2$O$_4$S.HCl (H$_2$O) C 57.53, H 7.44, N 5.59; Found C 57.12, H 7.30, N 5.80.

EXAMPLE 59

N-2-(4-((2-Hydroxy)-ethoxy)-phenyl)-propyl-2-propanesulfonamide

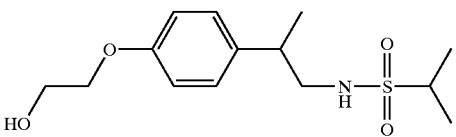

To a stirred mixture lithium aluminum hydride (1 mL, 1.0 mmol) in dry tetrahydrofuran (6 mL) was added N-2-(4-((2-carboxylic acid)-ethoxy)-phenyl)-propyl-2-propanesulfonamide (0.250 g, .60 mmol) at 0° C. and under nitrogen. The resulting mixture was stirred for 3 h and allowed to warm to ambient temperature. To the mixture was then added water (30 uL), 15% solution of sodium hydroxide (30 uL), and lastly another portion of water (100 uL) which was stirred at ambient temperature for 1 h. The resulting mixture was filtered over celite and the solvents evaporated in vacuo. The resulting product is added to a stirred mixture of dichloromethane: trifluoroacetic acid (2 mL, 1:1) under nitrogen. The resulting mixture was stirred at ambient temperature for 4 h. The mixture was partitioned between dichloromethane and 10% aqueous potassium carbonate. The organic layer was washed with brine (1×20 mL), dried over magnesium sulfate, and filtered. Evaporation of the filtrate in vacuo followed by chromatography on silica gel eluting with ethyl acetate-hexane gave 0.060 g (33%) of the title compound.

Mass Spectrum: MS$^{+1}$=302.2.

EXAMPLE 60

N-(2-((4-((Benzamido)methyl)oxy)phenyl)propyl)2-Propanesulfonamide

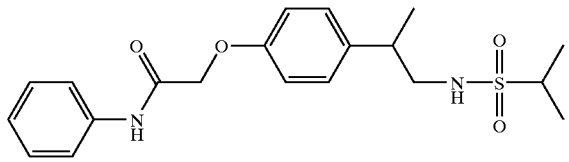

A solution of the acid from Preparation 17 (0.200 g, 0.48 mmol) in dry dimethylforamide (10 mL) was treated with aniline (0.05 mL, 0.58 mmol), Pip-Pip HOBT. (0.222 g, 0.58 mmol, preparation 18), and EDCI.HCl (0.120 g, 0.62 mmol). The resulting mixture was stirred at room temperature for 2 hour. The mixture was partitioned between dichloromethane and aqueous solution of HCl (10%). The organic layer was washed with water (2×10 mL) and brine (1×10 mL), dried over sodium sulfate, and filtered. Evaporation of the filtrate in vacuo gave the protected product which was treated with a 1:1 mixture of CH$_2$Cl$_2$:TFA (6 mL). The resulting mixture was stirred at room temperature for 12 hours. The mixture was partitioned between dichloromethane and aqueous solution of potassium carbonate. The organic layer was washed with water (2×10 mL) and brine (1×10 mL), dried over sodium sulfate, and filtered. Evaporation of the filtrate in vacuo to gave 0.152 g (81%) of the title compound.

Electrospray Mass Spectrum: 390.5; Analysis for C$_{20}$H$_{26}$N$_2$O$_4$S.

EXAMPLE 61

N-(2-((4-((4-Methylbenzamido)methyl)oxy)phenyl)propyl) 2-Propanesulfonamide

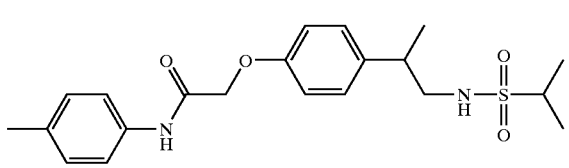

The title compound was prepared from the product of Preparation 17 (0.100 g, 0.24 mmol) and 4-methylaniline (0.03 mL, 0.29) in a manner analogous to the procedure described in Example 60.

Field Desorption Mass Spectrum: 404.5; Analysis for $C_{21}H_{28}N_2O_4S$:

EXAMPLE 62

N-(2-((4-((4-Isopropylbenzamido)methyl)oxy)phenyl)propyl) 2-Propanesulfonamide

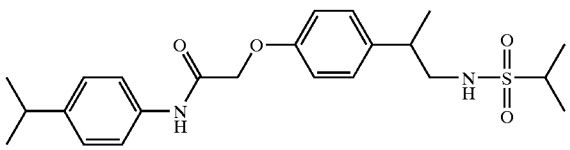

The title compound was prepared from the product of Preparation 17 (0.100 g, 0.24 mmol) and 4-isopropylaniline (0.04 mL, 0.29 mmol) in a manner analogous to the procedure described in Example 60.

Field Desorption Mass Spectrum: 432.6; Analysis for $C_{23}H_{32}N_2O_4S$: Theory: C, 63.86; H, 7.45; N, 6.47. Found C, 63.83; H, 7.59; N, 6.19.

EXAMPLE 63

N-(2-((4-((4-Methoxylbenzamido)methyl)oxy)phenyl)propyl) 2-Propanesulfonamide

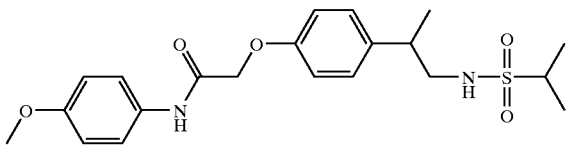

The title compound was prepared from the product of Preparation 17 (0.100 g, 0.24 mmol) and 4-isopropylanline (0.036 g, 0.29 mmol) in a manner analogous to the procedure described in Example 60.

Field Desorption Mass Spectrum: 420.5; Analysis for $C_{28}H_{28}N_2O_4S$: Theory: C, 59.98; H, 6.71; N, 6.66. Found C, 59.97; H, 6.78; N, 6.43.

EXAMPLE 64

N-(2-((4-((3,4-Difluorobenzamido)acetyl)oxy)phenyl)propyl) 2-Propanesulfonamide

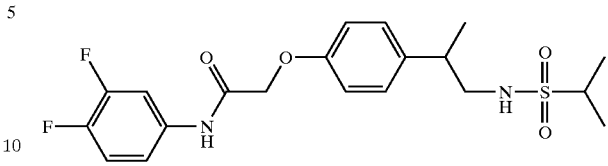

The title compound was prepared from the product of Preparation 17 (0.150 g, 0.36 mmol) and 3,4-difluoroaniline (0.040 g, 0.43 mmol) in a manner analogous to the procedure described in Example 60.

Field Desorption Mass Spectrum: 426.5.

EXAMPLE 65

Preparation of:

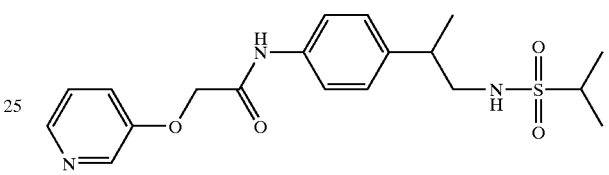

Into a 250 mL 3 necked flask fitted with a stirrer and thermometer, chloroacetyl chloride (0.971 g, 8.58 mmol) in 10 mL acetone was added dropwise to N-2-(4-aminophenyl)propyl 2-propanesulfonamide (2.00 g, 7.80 mmol, prepared in preparation 4) and $Na_2CO_3$ (0.910 g, 8.58 mmol) in 60 mL of acetone while stirring at room temperature under a nitrogen atmosphere. The reaction mixture was stirred at this temperature for one hour. The solution was filtered over a celite© mat and the resulting filtrate was concentrated under reduced vacuum to yield 3.00 g. of a white solid. This material was purified via silica gel chromatography employing the Water's prep. 2000 and eluting with a gradient solvent of methylene chloride to methylene chloride/ethyl acetate 9:1 over a 30 minute period to yield 2.16 g (84%) of the following chloro derivative:

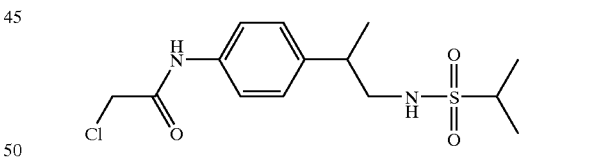

as a slowly crystallizing oil mp 137.5°–138.5° C. The NMR spectrum was consistent with the proposed structure. Ion spray M.S. 333.2 (M*+1).

Into a flame dried 250 mL 3 necked flask fitted with stirrer, thermometer, and condenser, 3-hydroxypyridine (0.062 g, 0.54 mmol) in 10 mL DMF was added dropwise to NaH(0.030 g, 0.75 mmol) in 20 mL DMF while stirring at room temperature under a nitrogen atmosphere. After stirring for 45 minutes at this temperature, the above prepared chloro derivative (0.150 g.0.45 mmol) in 20 mL DMF was added dropwise to the reaction followed by NaI(0.077 g, 0.51 mmol) added spatula-wise. The reaction mixture was then heated at 100° C. for 1.5 hours. The mixture was then cooled to room temperature and poured into 50 mL $H_2O$. The desired product was extracted with 50 mL ethyl acetate and the layers were separated. The organic layer was washed once with H₂O, dried over K₂CO₃, and concentrated under reduced vacuum to yield 0.181 g of an oil. This material was purified via silica gel chromatography employing the chromatotron using a 2000 micron rotor and eluting with a solvent ethyl acetate to yield 0.065 g (37%) of the title compound as a yellow oil. The NMR spectrum was consistent with the proposed structure. Ion spray M.S. 392.2 (M*+1).

EXAMPLE 66

Preparation of:

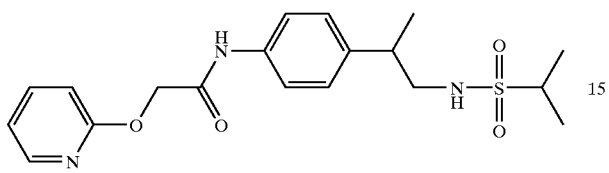

Into a flame dried 250 mL 3 necked flask fitted with stirrer, thermometer, and condenser, 2-hydroxypyridine (0.062 g, 0.540 mmol) in 10 mL DMF was added dropwise to NaH(0.030 g, 0.750 mmol) in 20 mL DMF while stirring at room temperature under a nitrogen atmosphere. After stirring for 45 minutes at this temperature, the chloro derivative prepared above in example 65 (0.150 g, 0.450 mmol) in 20 mL DMF was added dropwise to the reaction followed by. NaI (0.077 g, 0.510 mmol) added spatula-wise. The reaction mixture was then heated at 100° C. for 1.5 hours. The mixture was then cooled to room temperature and poured into 50 mL H₂O. The desired product was extracted with 50 mL ethyl acetate and the layers were separated. The organic layer was washed once with H₂O, dried over K₂CO₃, and concentrated under reduced vacuum to yield 0.190 g of a foam. This material was purified via silica gel chromatography employing the chromatotron using a 2000 micron rotor and eluting with ethyl acetate to yield 0.040 g (23%) of the title compound as a white solid, mp 176°–178° C. The NMR spectrum was consistent with the proposed structure. Ion spray M.S. 392.2 (M*+1); Analysis calculated for: $C_{19}H_{25}N_3O_4S$: Theory: C, 58.29 H, 6.44 N, 10.73; Found: C, 57.89 H, 6.12 N, 10.55.

EXAMPLE 67

Preparation of:

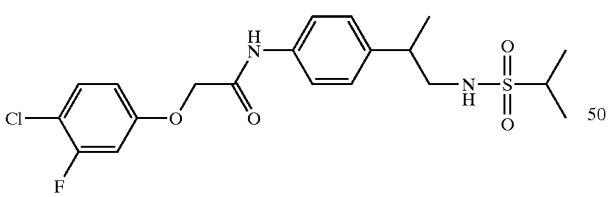

Into a flame dried 250 mL 3 necked flask fitted with stirrer, thermometer, and condenser, 4-chloro-3-fluorophenol (0.078 g, 0.54 mmol) in 10 mL DMF was added dropwise to NaH(0.030 g, 0.75 mmol) in 20 mL DMF while stirring at room temperature under a nitrogen atmosphere. After stirring for 45 minutes at this temperature, the chloro derivative prepared above in example 65 (0.150 g in 20 mL DMF) was added dropwise to the reaction followed by NaI (0.077 g, 0.51 mmol) added spatula wise. The reaction mixture was then heated at 100° C. for 1.5 hours. The mixture was then cooled to room temperature and poured into 50 mL H₂O. The desired product was extracted with 50 mL ethyl acetate and the layers were separated. The organic layer was washed once with H₂O, dried over K₂CO3, and concentrated under reduced vacuum to yield 0.201 g. of an oil. This material was purified via silica gel chromatography employing the chromatotron using a 2000 micron rotor and eluting with a solvent of methylene chloride/ethyl acetate 9:1 to yield 0.085 g (43%) of the title compound as a yellow oil. The NMR spectrum was consistent with the proposed structure. Ion spray M.S. 443.2 (M*+1).

EXAMPLE 68

Preparation of:

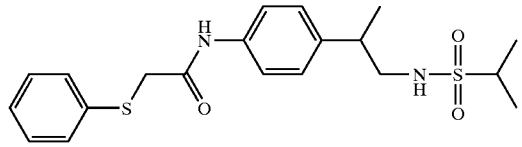

Into a flame dried 250 mL 3 necked flask fitted with stirrer, thermometer, and condenser, benzenethiol (0.096 g, 0.87 mmol) in 10 mL DMF was added dropwise to NaH (0.040 g, 1.00 mmol) in 20 mL DMF while stirring at room temperature under a nitrogen atmosphere. After stirring for 45 minutes at this temperature, the chloro derivative prepared in example 65 above (0.200 g, 0.60 mmol) in 20 mL DMF was added dropwise to the reaction followed by of NaI (0.102 g, 0.51 mmol) added spatula wise. The reaction mixture was then heated at 100° C. for 1.5 hours. The mixture was then cooled to room temperature and poured into 50 mL H₂O. The desired product was extracted with 50 mL ethyl acetate and the layers were separated. The organic layer was washed once with H₂O, dried over K₂CO₃, and concentrated under reduced vacuum to yield 0.317 g. of an oil. This material was purified via silica gel chromatography employing the chromatotron using a 4000 micron rotor and eluting with a solvent of hexane/ethyl acetate 1:1 to yield 0.100 g.(41%) of the title compound as a white solid The NMR spectrrum was consistent with the proposed structure. Ion spray M.S. 407.4 (M*+1). Analysis calculated for: $C_{20}H_{26}N_2O_3S_2$-1/2 H₂O: Theory: C, 57.79 H, 6.55 N, 6.74; Found: C, 57.84 H, 6.58 N, 6.66.

Particularly preferred combinations of

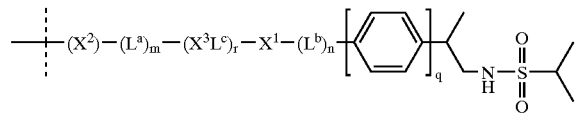

are shown in Table I and can be prepared using known techniques and procedures, and techniques and procedures described herein, by one of ordinary skill in the art. The reagents and starting materials are readily available to one of ordinary skill in the art.

TABLE I

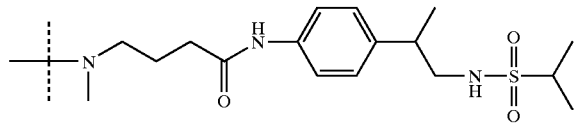

TABLE I-continued
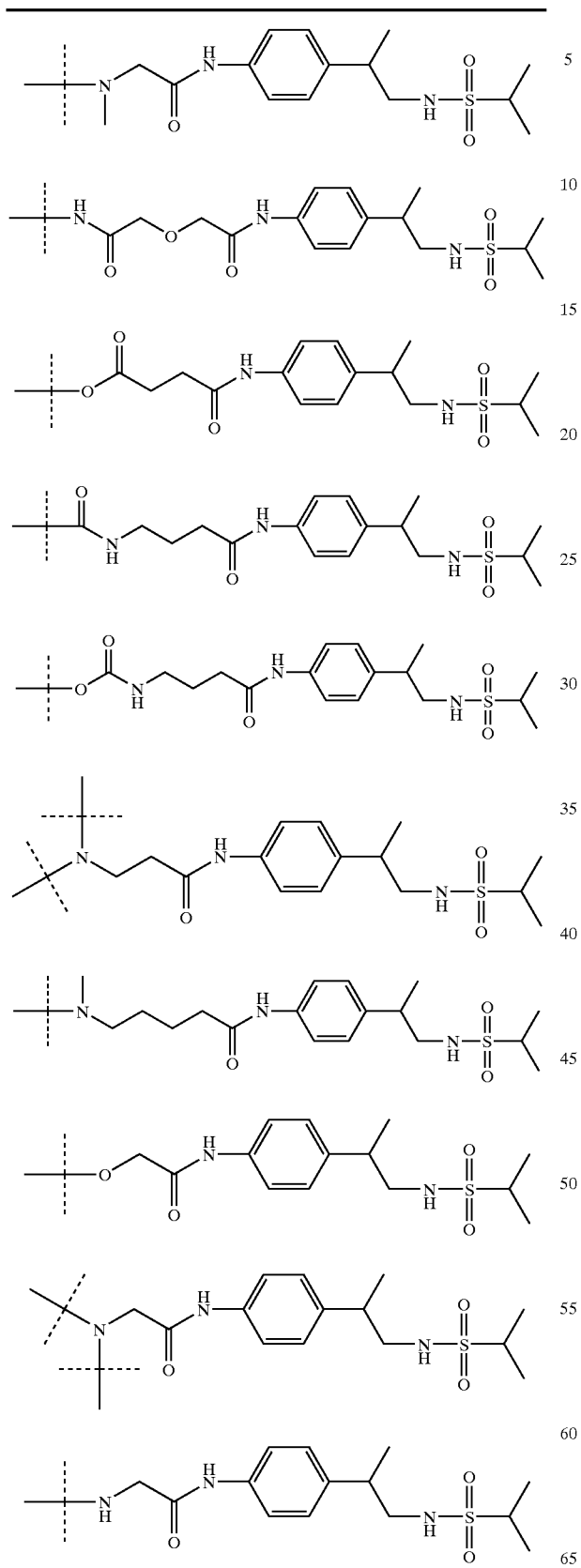
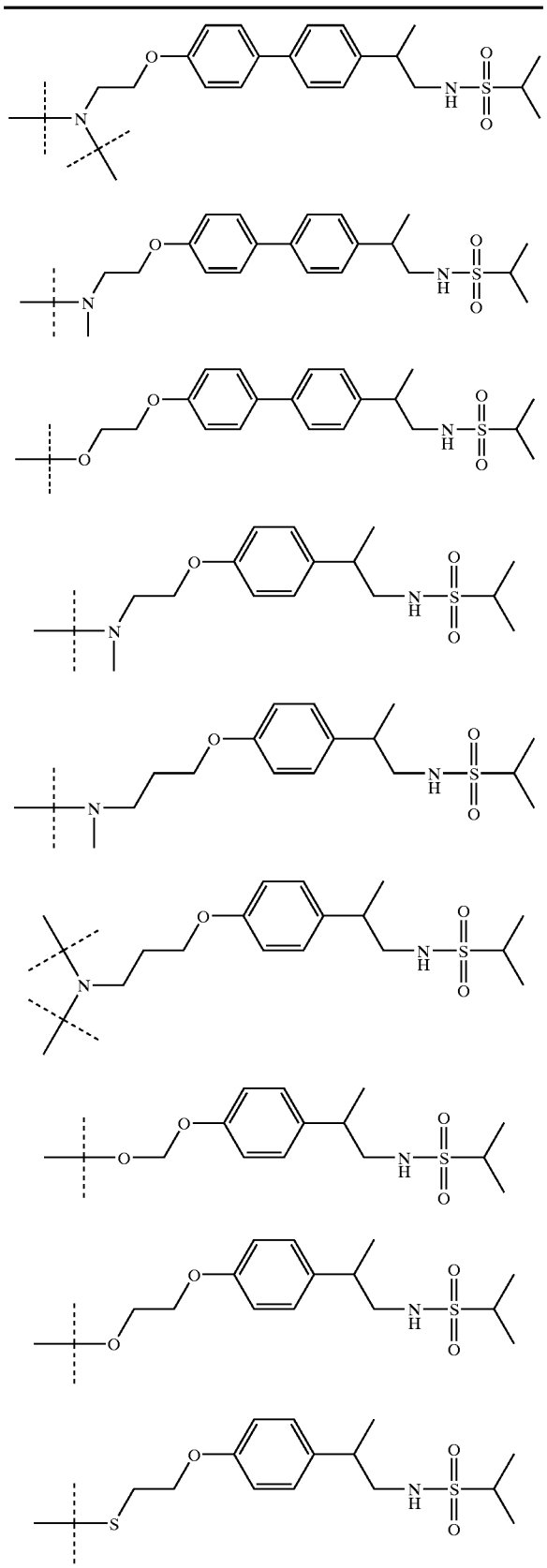

51

TABLE I-continued

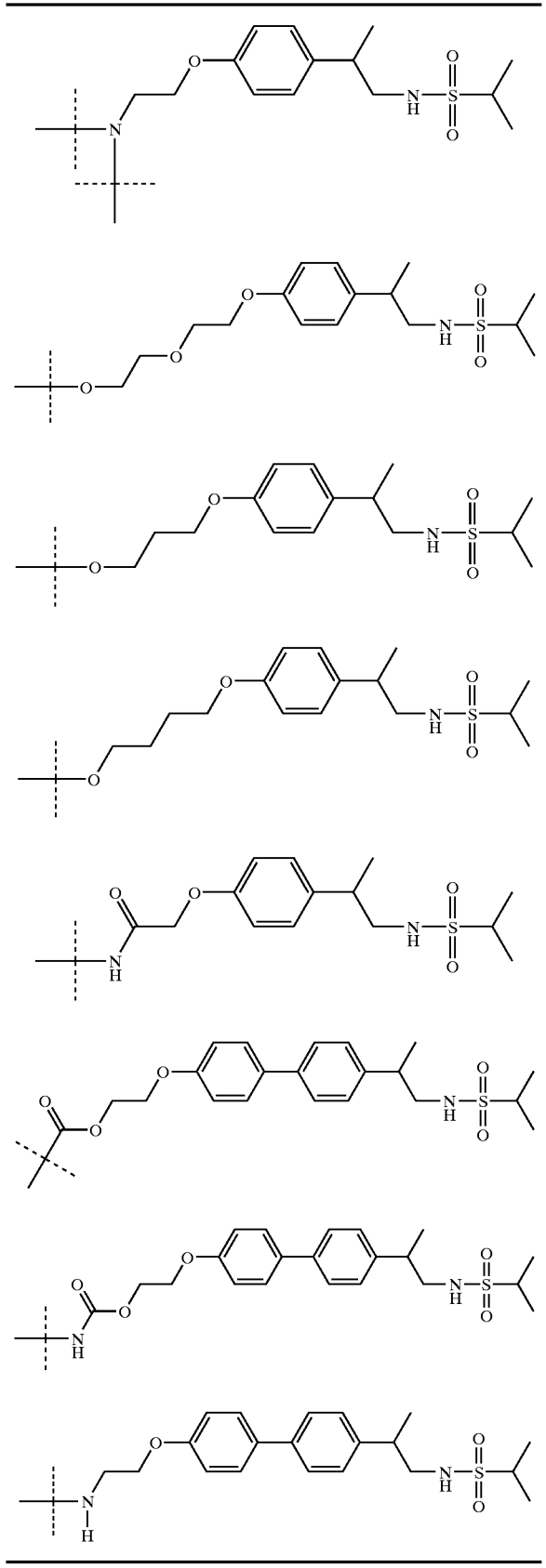

52

We claim:
1. A compound of the formula:

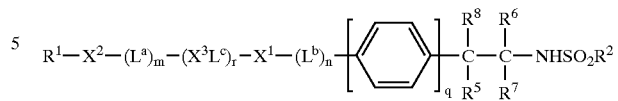

wherein:
L$^a$ represents (1–4C)alkylene;
L$^b$ represents (1–4C)alkylene;
L$^c$ represents (1–4C)alkylene;
r is zero or 1;
m is zero or 1;
n is zero;
q is 1 or 2;
X$^1$ represents O or CONH;
X$^2$ represents O, S, NR$^{10}$, C(=O), OCO, COO, NHCO$_2$, O$_2$CNH, CONH, NHCO, SO or SO$_2$;
X$^3$ represents O, S, NR$^{11}$, C(=O), NHCO$_2$, O$_2$CNH, CONH, NHCO, SO or SO$_2$;
R$^1$ represents a hydrogen atom, a (1–4C)alkyl group, a (3–8C)cycloalkyl group, an optionally substituted aromatic group, an optionally substituted heteroaromatic group, or a saturated 4 to 7 membered heterocyclic ring containing the group NR$^{10}$ and a group X as the only hetero ring members, wherein X represents —CH$_2$—, CO, O, S or NR$^{12}$ and R$^{12}$ represents hydrogen or (1–4C);
R$^9$ is hydrogen or (1–4C)alkyl;
R$^{10}$ is hydrogen or (1–4C)alkyl, or
R$^1$ and R$^{10}$ together with the nitrogen atom to which they are attached form an azetidinyl, pyrrolidinyl, piperidinyl, 4-di(1–4C)alkylaminopiperidinyl, morpholino, piperazinyl or N-(1–4C)alkylpiperazinyl group;
R$^{11}$ is hydrogen or (1–4C)alkyl;
R$^2$ represents 2-propyl;
R$^5$, R$^6$ and R$^7$ each represent hydrogen;
R$^8$ represents methyl;
or a pharmaceutically acceptable salt thereof,
provided that (1) if m represents zero, then X$^1$ represents CONH, X$^2$ represents NR$^{10}$ and R$^1$ and R$^{10}$ together with the nitrogen atom to which they are attached form an azetidinyl, piperidinyl, 4-di(1–4C)alkylaminopiperidinyl, piperazinyl or N-(1–4C)alkylpiperazinyl group, and (2) if the group —X$^2$—(L$^a$)$_m$—(X$^3$L$^c$)$_r$—X$^1$—(L$^b$)$_n$— represents —OCH$_2$CONH—, then R$^1$ does not represent an optionally substituted aromatic group or an optionally substituted heteroaromatic group.

2. A compound as claimed in claim 1, wherein X$^2$ represents O, NR$^{10}$ wherein R$^{10}$ represents hydrogen, methyl or, together with R$^1$, pyrrolidinyl, piperidinyl, 4-(N, N-dimethylamino)piperidinyl or N-methylpiperazinyl, NHCO, CONH, OCO or OCONH; X$^3$ represents O; L$^a$ represents methylene, ethylene, propylene or butylene; L$^c$ represents methylene; and m represents 1.

3. A compound as claimed in claim 2, wherein R$^1$ represents hydrogen, methyl, ethyl, propyl, t-butyl, cyclohexyl, phenyl, 4-isopropylphenyl, 4-methoxyphenyl, 3-cyanophenyl, 4-cyanophenyl, 2-fluorophenyl, 3-fluorophenyl, 4-fluorophenyl, 4-chlorophenyl, 2-trifluoromethylphenyl, 3-trifluoromethylphenyl, 4-trifluoromethylphenyl, 2-acetamidophenyl, 3-acetamidophenyl, 4-acetamidophenyl and, together with $X^2$ when it represents $NR^{10}$, pyrrolidinyl, piperidinyl, 4-(N, N-dimethylamino)-piperidinyl or N-methylpiperazinyl.

4. A pharmaceutical composition, which comprises a compound as claimed in claim 1 and a pharmaceutically acceptable diluent or carrier.

5. A method of potentiating glutamate receptor function in a mammal requiring such treatment, which comprises administering an effective amount of a compound of the formula:

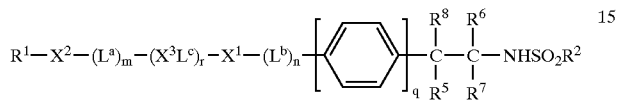

wherein:

$L^a$ represents (1–4C)alkylene;

$L^b$ represents (1–4C)alkylene;

$L^c$ represents (1–4C)alkylene;

r is zero or 1;

m is zero or 1;

n is zero;

q is 1 or 2;

$X^1$ represents O, or CONH;

$X^2$ represents O, S, $NR^{10}$, C(=O), OCO, COO, $NHCO_2$, $O_2CNH$, CONH, NHCO, SO or $SO_2$;

$X^3$ represents O, S, $NR^{11}$, C(=O), $NHCO_2$, $O_2CNH$, CONH, NHCO, SO or $SO_2$;

$R^1$ represents a hydrogen atom, a (1–4C)alkyl group, a (3–8C)cycloalkyl group, an optionally substituted aromatic group, an optionally substituted heteroaromatic group, or a saturated 4 to 7 membered heterocyclic ring containing the group $NR^{10}$ and a group X as the only hetero ring members, wherein X represents —$CH_2$—, CO, O, S or $NR^{12}$ and $R^{12}$ represents hydrogen or (1–4C);

$R^9$ is hydrogen or (1–4C)alkyl;

$R^{10}$ is hydrogen or (1–4C)alkyl, or $R^1$ and $R^{10}$ together with the nitrogen atom to which they are attached form an azetidinyl, pyrrolidinyl, piperidinyl, 4-di(1–4C)alkylaminopiperidinyl, morpholino, piperazinyl or N-(1–4C)alkylpiperazinyl group;

$R^{11}$ is hydrogen or (1–4C)alkyl;

$R^2$ represents 2-propyl;

$R^5$, $R^6$ and $R^7$ each represent hydrogen; and $R^8$ represents methyl;

or a pharmaceutically acceptable salt thereof, provided that (1) if m represents zero, then $X^1$ represents CONH, $X^2$ represents $NR^{10}$ and $R^1$ and $R^{10}$ together with the nitrogen atom to which they are attached form an azetidinyl, piperidinyl, 4-di(1–4C)alkylaminopiperidinyl, piperazinyl or N-(1–4C)alkylpiperazinyl group, and (2) if the group

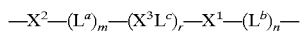

represents —$OCH_2CONH$—, then $R^1$ does not represent an optionally substituted aromatic group or an optionally substituted heteroaromatic group.

6. A method of treating a cognitive disorder; a neurodegenerative disorder; age-related dementia; age-induced memory impairment; a movement disorder; reversal of drug-induced states; depression; attention deficit disorder; attention deficit hyperactivity disorder; psychosis; cognitive deficits associated with psychosis; or drug-induced psychosis in a patient, which comprises administering to a patient in need thereof an effective amount of a compound of the formula:

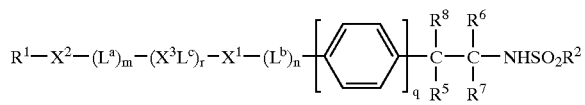

wherein:

$L^a$ represents (1–4C)alkylene;

$L^b$ represents (1–4C)alkylene;

$L^c$ represents (1–4C)alkylene;

r is zero or 1;

m is zero or 1;

n is zero;

q is 1 or 2;

$X^1$ represents O or CONH;

$X^2$ represents O, S, $NR^{10}$, C(=O), OCO, COO, $NHCO_2$, $O_2CNH$, CONH, NHCO, SO or $SO_2$;

$X^3$ represents O, S, $NR^{11}$, C(=O), $NHCO_2$, $O_2CNH$, CONH, NHCO, SO or $SO_2$;

$R^1$ represents a hydrogen atom, a (1–4C)alkyl group, a (3–8C)cycloalkyl group, an optionally substituted aromatic group, an optionally substituted heteroaromatic group, or a saturated 4 to 7 membered heterocyclic ring containing the group $NR^{10}$ and a group X as the only hetero ring members, wherein X represents —$CH_2$—, CO, O, S or $NR^{12}$ and $R^{12}$ represents hydrogen or (1–4C);

$R^9$ is hydrogen or (1–4C)alkyl;

$R^{10}$ is hydrogen or (1–4C)alkyl, or $R^1$ and $R^{10}$ together with the nitrogen atom to which they are attached form an azetidinyl, pyrrolidinyl, piperidinyl, 4-di(1–4C)alkylaminopiperidinyl, morpholino, piperazinyl or N-(1–4C)alkylpiperazinyl group;

$R^{11}$ is hydrogen or (1–4C)alkyl;

$R^2$ represents 2-propyl;

$R^5$, $R^6$ and $R^7$ each represent hydrogen; and $R^8$ represents methyl;

or a pharmaceutically acceptable salt thereof, provided that (1) if m represents zero, then $X^1$ represents CONH, $X^2$ represents $NR^{10}$ and $R^1$ and $R^{10}$ together with the nitrogen atom to which they are attached form an azetidinyl, piperidinyl, 4-di(1–4C)alkylaminopiperidinyl, piperazinyl or N-(1–4C)alkylpiperazinyl group, and (2) if the group

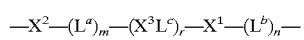

represents —$OCH_2CONH$—, then $R^1$ does not represent an optionally substituted aromatic group or an optionally substituted heteroaromatic group.

7. A method for improving memory or learning ability in a patient, which comprises administering to a patient in need thereof an effective amount of a compound of the formula:

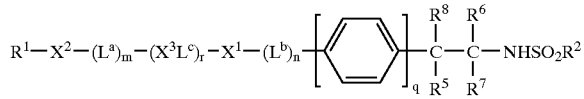

wherein:
$L^a$ represents (1–4C)alkylene;
$L^b$ represents (1–4C)alkylene;
$L^c$ represents (1–4C)alkylene;
r is zero or 1;
m is zero or 1;
n is zero;
q is 1 or 2;
$X^1$ represents O, or CONH;
$X^2$ represents O, S, $NR^{10}$, C(=O), OCO, COO, $NHCO_2$, $O_2CNH$, CONH, NHCO, SO or $SO_2$;
$X^3$ represents O, S, $NR^{11}$, C(=O), $NHCO_2$, $O_2CNH$, CONH, NHCO, SO or $SO_2$;
$R^1$ represents a hydrogen atom, a (1–4C)alkyl group, a (3–8C)cycloalkyl group, an optionally substituted aromatic group, an optionally substituted heteroaromatic group, or a saturated 4 to 7 membered heterocyclic ring containing the group $NR^{10}$ and a group X as the only hetero ring members, wherein X represents —$CH_2$—, CO, O, S or $NR^{12}$ and $R^{12}$ represents hydrogen or (1–4C);
$R^9$ is hydrogen or (1–4C)alkyl;
$R^{10}$ is hydrogen or (1–4C)alkyl, or
$R^1$ and $R^{10}$ together with the nitrogen atom to which they are attached form an azetidinyl, pyrrolidinyl, piperidinyl, 4-di(1–4C)alkylaminopiperidinyl, morpholino, piperazinyl or N-(1–4C)alkylpiperazinyl group;
$R^{11}$ is hydrogen or (1–4C)alkyl;
$R^2$ represents 2-propyl;
$R^5$, $R^6$ and $R^7$ each represent hydrogen; and
$R^8$ represents methyl;
or a pharmaceutically acceptable salt thereof,
provided that (1) if m represents zero, then $X^1$ represents CONH, $X^2$ represents $NR^{10}$ and $R^1$ and $R^{10}$ together with the nitrogen atom to which they are attached form an azetidinyl, piperidinyl, 4-di(1–4C)alkylaminopiperidinyl, piperazinyl or N-(1–4C)alkylpiperazinyl group, and (2) if the group

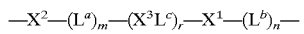

represents —$OCH_2CONH$—, then $R^1$ does not represent an optionally substituted aromatic group or an optionally substituted heteroaromatic group.

8. A compound according to claim 1 wherein m is 1.

9. A compound according to claim 8 wherein $L^a$ is methylene, ethylene, propylene, or butylene.

10. A compound according to claim 9 wherein q is 1.

11. A compound according to claim 9 wherein q is 2.

12. A compound selected from the group consisting of:
N-2-[4-((3-N,N-dimethylaminopropyl)-carboxamido)phenyl]propyl 2-propanesulfonamide;
N-2-[4-(N,N-dimethylglycinamido)phenyl]propyl 2-propanesulfonamide;
N-2-[4-(aminocarbonylmethoxyacetamido)phenyl]propyl 2-propanesulfonamide;
N-2-[4-(3-methoxycarbonylpropanoyl)amido)-phenyl]propyl 2-propanesulfonamide;
N-2-[4-(4-acetamido)butanoylamido)phenyl]-propyl-2-propanesulfonamide;
N-2-[4-(4-(t-butoxycarbonylamino)-butanoylamido)phenyl]propyl 2-propanesulfonamide;
N-2-[4-(3-piperidinylpropanoylamido)-phenyl]propyl 2-propanesulfonamide;
N-2-[4-(5-N,N-dimethylamino)pentanoylamido)phenyl]propyl 2-propanesulfonamide;
N-2-[4-(3-N-cyclohexylamino)-propanoylamido)phenyl]propyl 2-propanesulfonamide;
N-2-[4-(2-ethoxy)acetamido)phenyl]propyl 2-propanesulfonamide;
N-2-[4-(2-methoxyacetamido)phenyl]propyl 2-propanesulfonamide;
N-2-[4-(2-butoxyacetamido)phenyl]propyl 2-propanesulfonamide;
N-2-[4-(1-(4-methyl)piperazinyl)acetamido)phenyl]propyl 2-propanesulfonamide;
N-2-[4-(1-piperidinylacetamido)-phenyl]propyl 2-propanesulfonamide; N-2-[4-(1-(4-N,N-dimethylamino)piperidinyl)acetamido-(phenyl]propyl 2-propanesulfonamide;
N-2-(4-(4-(2-(1-pyrrolidino)ethoxy)phenyl)phenyl) propyl 2-propanesulfonamide;
N-2-(4-(4-(2-(N,N-dimethylamino)ethoxy)phenyl) phenyl)propyl-2-propanesulfonamide;
N-2-(4-(4-(2-hydroxy)ethoxy)phenyl)phenyl)propyl 2-propanesulfonamide;
N-2-[4-(2-(N,N-dimethylamino)ethoxy)phenyl]propyl 2-propanesulfonamide;
N-2-[4-(3-(N,N-dimethylamino)propoxy)phenyl]propyl 2-propanesulfonamide;
N-2-([4-(2-(1-piperidinyl)ethoxy)phenyl]propyl-2-propanesulfonamide;
N-2-[4-(3-(1-piperidinyl)propoxy)phenyl]propyl 2-propanesulfonamide;
N-2-[4-(4-chlorophenoxymethyl)oxy)phenyl]propyl 2-propanesulfonamide;
N-2-[4-(2-phenoxyethyl)oxy)phenyl]propyl 2-propanesulfonamide;
N-2-[4-(2-(4-acetamido)phenyloxyethoxy)phenyl]propyl 2-propanesulfonamide;
N-2-[4-(2-(3-acetamido)phenyloxyethoxy)phenyl]propyl 2-propanesulfonamide;
N-2-[4-((2-acetamido)phenyloxyethoxy)phenyl]propyl 2-propanesulfonamide;
N-2-(4-(2-phenoxyethoxy)-phenyl)-propyl-2-propanesulfonamide;
N-2-(4-(2-(2-acetamidophenoxy)-ethoxy)-phenyl)-propyl-2-propanesulfonamide;
N-2-(4-(2-(2-fluorophenoxy)-ethoxy)-phenyl)-propyl-2-propanesulfonamide;
N-2-(4-(2-(3-fluorophenoxy)-ethoxy)-phenyl)-propyl-2-propanesulfonamide;
N-2-(4-(2-(4-fluorophenoxy)-ethoxy)-phenyl)-propyl-2-propanesulfonamide;
N-2-(4-(2-(3-trifluoromethylphenoxy)-ethoxy)-phenyl)-propyl-2-propanesulfonamide;

N-2-(4-(2-(4-trifluoromethylphenoxy)-ethoxy)-phenyl)-propyl-2-propanesulfonamide;
N-2-(4-(2-(2,3-difluorophenoxy)-ethoxy)-phenyl)-propyl-2-propanesulfonamide;
N-2-(4-(2-(2-cyanophenoxy)-ethoxy)-phenyl)-propyl-2-propanesulfonamide;
N-2-(4-(2-(3-cyanophenoxy)-ethoxy)-phenyl)-propyl-2-propanesulfonamide;
N-2-(4-(2-(4-cyanophenoxy)-ethoxy)-phenyl)-propyl-2-propanesulfonamide;
N-2-[(4-(2-(2-chlorophenoxy)-ethoxy)-phenyl)-propyl]-2-propanesulfonamide;
N-2-(4-(2-(2-methoxyphenoxy)-ethoxy)-phenyl)-propyl-2-propanesulfonamide;
N-2-[(4-(2-(2-fluorothiophenoxy)-ethoxy)-phenyl)-propyl]-2-propanesulfonamide;
N-2-[(4-(2-(thiophenoxy)-ethoxy)-phenyl)-propyl]-2-propanesulfonamide;
N-2-(4-(2-(3-pyridyloxy)-ethoxy)-phenyl)-propyl-2-propanesulfonamide;
N-2-(4-(2-(N'-2-pyridinone)-ethoxy)-phenyl)-propyl-2-propanesulfonamide;
N-2-(4-(2-(2-pyrimidyloxy)-ethoxy)-phenyl)-propyl-2-propanesulfonamide;
N-2-(4-(2-(methoxy)-ethoxy)-phenyl)-propyl-2-propanesulfonamide;
N-2-(4-(2-(ethoxy)-ethoxy)-phenyl)-propyl-2-propanesulfonamide;
N-2-(4-(2-(2-methoxyethoxy)-ethoxy)-phenyl)-propyl-2-propanesulfonamide;
N-2-(4-(3-(phenoxy)-propoxy)-phenyl)-propyl-2-propanesulfonamide;
N-2-(4-(3-(phenoxy)-butoxy)-phenyl)-propyl-2-propanesulfonamide;
N-2-(4-(4-(2-acetoxyethyl)phenoxy)phenyl)propyl-2-propanesulfonamide;
N-2-(4-(4-(2-(N-phenylcarbamoyl)ethyl)phenoxy)propyl-2-propanesulfonamide;
N-2-(4-(4-(2-(N-ethylcarbamoyl)ethyl)phenoxy)propyl-2-propanesulfonamide;
N-2-(4-(4-(2-(O-methanesulfonyl)ethyl)phenoxy)propyl-2-propanesulfonamide;
N-2-(4-(4-(2-azidoethyl)phenoxy)propyl-2-propanesulfonamide;
N-2-(4-(4-(2-aminoethyl)phenoxy)propyl-2-propanesulfonamide hydrochloride;
N-2-(4-(4-(2-(4-N-morpholino)ethyl)phenoxy)phenyl)propyl-2-propanesulfonamide;
N-2-(4-((2-hydroxy)-ethoxy)-phenyl)-propyl-2-propanesulfonamide;
N-(2-((4-((benzamido)methyl)oxy)phenyl)propyl) 2-propanesulfonamide;
N-(2-((4-((4-methylbenzamido)methyl)oxy)phenyl)propyl) 2-propanesulfonamide;
N-(2-((4-((4-isopropylbenzamido)methyl)oxy)phenyl)propyl) 2-propanesulfonamide;
N-(2-((4-((4-methoxybenzamido)methyl)oxy)phenyl)propyl) 2-propanesulfonamide; and
N-(2-((4-((3,4-difluorobenzamido)acetyl)oxy)phenyl)propyl) 2-propanesulfonamide;

and the pharmaceutically acceptable salts thereof.

13. A compound selected from the group consisting of:

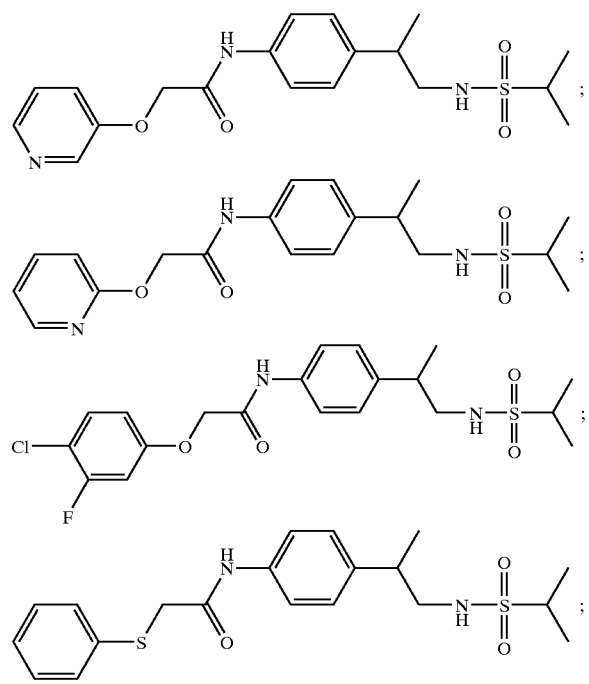

and the pharmaceutically acceptable salts thereof.

* * * * *